US011826172B2

(12) United States Patent
Marrs et al.

(10) Patent No.: US 11,826,172 B2
(45) Date of Patent: Nov. 28, 2023

(54) ELECTRODE SUPPORT STRUCTURE ASSEMBLY

(71) Applicant: St. Jude Medical, Cardiology Division, Inc., St. Paul, MN (US)

(72) Inventors: James C. Marrs, Arden Hills, MN (US); Neil D. Hawkinson, Ramsey, MN (US); Brian M. Monahan, Elk River, MN (US); Dale E. Just, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 812 days.

(21) Appl. No.: 15/308,582

(22) PCT Filed: Apr. 30, 2015

(86) PCT No.: PCT/US2015/028502
§ 371 (c)(1),
(2) Date: Nov. 2, 2016

(87) PCT Pub. No.: WO2015/171418
PCT Pub. Date: Nov. 12, 2015

(65) Prior Publication Data
US 2017/0065227 A1    Mar. 9, 2017

Related U.S. Application Data

(60) Provisional application No. 61/989,230, filed on May 6, 2014.

(51) Int. Cl.
*A61B 18/14*    (2006.01)
*A61B 5/00*     (2006.01)
(Continued)

(52) U.S. Cl.
CPC ............ *A61B 5/6858* (2013.01); *A61B 5/283* (2021.01); *A61B 5/287* (2021.01); *A61B 17/221* (2013.01);
(Continued)

(58) Field of Classification Search
CPC ..... A61B 5/6858; A61B 5/042; A61B 5/0422; A61B 17/221; A61B 2017/2212;
(Continued)

(56) References Cited

U.S. PATENT DOCUMENTS 5,224,939 A    7/1993   Holman et al.
5,380,301 A    1/1995   Prichard et al.
(Continued)

FOREIGN PATENT DOCUMENTS

CN    103517682 A    1/2014
CN    101927053 B    1/2015
(Continued)

*Primary Examiner* — Eun Hwa Kim
*Assistant Examiner* — Catherine Premraj
(74) *Attorney, Agent, or Firm* — Kilpatrick Townsend & Stockton LLP

(57) ABSTRACT

An electrode support structure assembly in a body in accordance with one embodiment of the present teachings includes a plug defining a longitudinal axis. The plug includes a lumen extending in an axial direction and including an axial distal end and a distal tip adjacent to the axial distal end of the lumen and including a first channel. The assembly further includes a cap disposed around at least a portion of the plug and including a plurality of apertures and an interior. The assembly further includes a plurality of support members, each support member comprising a distal portion. The cap is configured to constrain relative movement of the distal portions of the plurality of support members with respect to the cap, and the first channel of the plug and at least one of the plurality of support members are
(Continued)

configured to direct a fluid after exiting the lumen of the plug.

19 Claims, 17 Drawing Sheets

(51) Int. Cl.
  *A61B 5/283* (2021.01)
  *A61B 5/287* (2021.01)
  *A61B 17/221* (2006.01)
  *A61B 18/00* (2006.01)
(52) U.S. Cl.
  CPC .............. *A61B 18/1492* (2013.01);
    *A61B 2018/00029* (2013.01); *A61B 2018/00267* (2013.01); *A61B 2018/00404* (2013.01); *A61B 2018/00577* (2013.01); *A61B 2218/002* (2013.01)
(58) Field of Classification Search
  CPC ...... A61B 18/1492; A61B 2018/00029; A61B 2018/00267; A61B 2018/00404; A61B 2018/00577; A61B 2018/00011; A61B 2218/002; A61B 5/283; A61B 5/287
  See application file for complete search history.

(56) References Cited

U.S. PATENT DOCUMENTS

| | | | |
|---|---|---|---|
| 5,400,783 A | 3/1995 | Pomeranz et al. | |
| 5,456,254 A | 10/1995 | Pietroski et al. | |
| 5,471,982 A | 12/1995 | Edwards et al. | |
| 5,626,136 A | 5/1997 | Webster, Jr. | |
| 5,715,817 A | 2/1998 | Stevens-Wright et al. | |
| 5,715,832 A | 2/1998 | Koblish et al. | |
| 5,772,590 A | 6/1998 | Webster, Jr. | |
| 5,827,278 A | 10/1998 | Webster, Jr. | |
| 5,876,373 A | 3/1999 | Giba et al. | |
| 5,893,847 A * | 4/1999 | Kordis .............. A61B 5/0422 600/41 |
| 6,074,379 A | 6/2000 | Prichard | |
| 6,273,404 B1 | 8/2001 | Holman et al. | |
| 6,491,681 B1 | 12/2002 | Kunis et al. | |
| 6,554,794 B1 | 4/2003 | Mueller et al. | |
| 7,004,937 B2 | 2/2006 | Lentz et al. | |
| 7,214,220 B2 | 5/2007 | McGlinch et al. | |
| 7,217,256 B2 | 5/2007 | Di Palma | |
| 7,522,950 B2 | 4/2009 | Fuimaono et al. | |
| 7,608,063 B2 | 10/2009 | Le et al. | |
| 7,625,365 B2 | 12/2009 | McGlinch et al. | |
| 7,666,204 B2 | 2/2010 | Thornton et al. | |
| 7,959,601 B2 | 6/2011 | McDaniel et al. | |
| 7,985,215 B2 | 7/2011 | Guo et al. | |
| 8,103,327 B2 | 1/2012 | Harlev et al. | |
| 8,137,321 B2 | 3/2012 | Argentine | |
| 8,221,390 B2 | 7/2012 | Pal et al. | |
| 8,273,016 B2 | 9/2012 | O'sullivan | |
| 8,376,990 B2 | 2/2013 | Ponzi et al. | |
| 8,447,377 B2 | 5/2013 | Harlev et al. | |
| 8,588,885 B2 | 11/2013 | Hall et al. | |
| 8,608,703 B2 | 12/2013 | Riles et al. | |
| 8,649,880 B1 | 2/2014 | Parker, Jr. | |
| 8,676,290 B2 | 3/2014 | Tegg | |
| 8,700,120 B2 | 4/2014 | Koblish | |
| 8,706,193 B2 | 4/2014 | Govari et al. | |
| 8,755,861 B2 | 6/2014 | Harlev et al. | |
| 8,777,929 B2 | 7/2014 | Schneider et al. | |
| 8,792,962 B2 | 7/2014 | Esguerra et al. | |
| 8,814,824 B2 | 8/2014 | Kauphusman et al. | |
| 8,814,825 B2 | 8/2014 | Tegg et al. | |
| 8,882,705 B2 | 11/2014 | McDaniel et al. | |
| 8,894,610 B2 | 11/2014 | Macnamara et al. | |
| 8,996,091 B2 | 3/2015 | de la Rama et al. | |
| 9,017,308 B2 | 4/2015 | Klisch et al. | |
| 9,033,917 B2 | 5/2015 | Magana et al. | |
| 9,050,010 B2 | 6/2015 | Bui et al. | |
| 9,101,733 B2 | 8/2015 | McDaniel | |
| 9,204,929 B2 | 12/2015 | Solis | |
| 9,216,056 B2 | 12/2015 | Datta et al. | |
| 9,247,990 B2 | 2/2016 | Kauphusman et al. | |
| 9,326,815 B2 | 5/2016 | Watson | |
| 9,339,631 B2 | 5/2016 | Graham et al. | |
| 9,433,751 B2 | 9/2016 | Ponzi et al. | |
| 9,433,752 B2 | 9/2016 | Jimenez et al. | |
| 9,468,495 B2 | 10/2016 | Kunis et al. | |
| 9,486,280 B2 | 11/2016 | Koblish et al. | |
| 9,486,282 B2 | 11/2016 | Solis | |
| 9,539,413 B2 | 1/2017 | Ogle | |
| 9,649,158 B2 | 5/2017 | Datta et al. | |
| 9,687,166 B2 | 6/2017 | Subramaniam et al. | |
| 9,694,159 B2 | 7/2017 | Schneider et al. | |
| 9,694,161 B2 | 7/2017 | Selkee | |
| 9,788,895 B2 | 10/2017 | Solis | |
| 9,919,132 B2 | 3/2018 | Tegg et al. | |
| 9,986,949 B2 | 6/2018 | Govari et al. | |
| 10,004,877 B2 | 6/2018 | Tegg | |
| 10,034,637 B2 | 7/2018 | Harlev et al. | |
| 10,052,457 B2 | 8/2018 | Nguyen et al. | |
| 10,065,019 B2 | 9/2018 | Hamuro et al. | |
| 10,143,394 B2 | 12/2018 | Solis | |
| 10,384,036 B2 | 8/2019 | Romoscanu | |
| 10,398,500 B2 | 9/2019 | Huszar et al. | |
| 10,575,745 B2 | 3/2020 | Solis | |
| 10,646,692 B2 | 5/2020 | Tegg et al. | |
| 10,653,423 B2 | 5/2020 | Starnes | |
| 10,835,712 B2 | 11/2020 | Wada | |
| 10,842,990 B2 | 11/2020 | de la Rama et al. | |
| 10,857,349 B2 | 12/2020 | de la Rama et al. | |
| 10,898,685 B2 | 1/2021 | Tegg | |
| 11,160,482 B2 | 11/2021 | Solis | |
| 11,272,886 B2 | 3/2022 | Harlev et al. | |
| 2002/0165484 A1 | 11/2002 | Bowe et al. | |
| 2008/0249522 A1* | 10/2008 | Pappone .............. A61M 25/003 606/41 |
| 2008/0312521 A1 | 12/2008 | Solomon | |
| 2009/0171274 A1 | 7/2009 | Harlev et al. | |
| 2010/0057074 A1* | 3/2010 | Roman .............. A61B 18/1492 606/33 |
| 2012/0143298 A1 | 6/2012 | Just et al. | |
| 2012/0271135 A1* | 10/2012 | Burke ................ A61B 5/6858 600/373 |
| 2013/0172715 A1* | 7/2013 | Just .................... A61B 18/1492 600/374 |
| 2013/0317375 A1 | 11/2013 | Garcia et al. | |
| 2014/0100639 A1 | 4/2014 | Lee et al. | |
| 2015/0119911 A1 | 4/2015 | Mckenzie | |
| 2016/0213423 A1 | 7/2016 | Kauphusman et al. | |
| 2020/0138378 A1 | 5/2020 | de la Rama et al. | |
| 2020/0253496 A1 | 8/2020 | Deno et al. | |
| 2021/0145342 A1 | 5/2021 | Wang | |
| 2022/0023594 A1 | 1/2022 | Pai | |
| 2022/0054066 A1 | 2/2022 | Solis | |

FOREIGN PATENT DOCUMENTS

| | | |
|---|---|---|
| CN | 103157168 B | 4/2015 |
| CN | 104434083 B | 4/2019 |
| CN | 104968261 B | 5/2019 |
| CN | 105592778 B | 7/2019 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2604306 B1 | 1/2014 |
| EP | 2915555 A1 | 9/2015 |
| EP | 1968679 B1 | 9/2016 |
| EP | 2241279 B1 | 9/2016 |
| EP | 3115076 A4 | 10/2017 |
| EP | 3117863 A4 | 10/2017 |

(56) References Cited

FOREIGN PATENT DOCUMENTS

| | | |
|---|---|---|
| EP | 3057488 B1 | 5/2018 |
| EP | 2848226 B1 | 7/2018 |
| EP | 3391928 A1 | 10/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 3466363 A1 | 4/2019 |
| EP | 2550989 B1 | 6/2019 |
| EP | 2569040 B1 | 12/2019 |
| EP | 2908723 B1 | 3/2020 |
| EP | 3738508 A1 | 11/2020 |
| EP | 3738509 A1 | 11/2020 |
| EP | 2155301 B1 | 4/2021 |
| EP | 2809254 B1 | 6/2021 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |
| JP | 2017051211 A | 3/2017 |
| JP | 6246742 B2 | 12/2017 |
| JP | 6434495 B2 | 12/2018 |
| JP | 6445509 B2 | 12/2018 |
| JP | 6515084 B2 | 4/2019 |
| JP | 6466114 B2 | 12/2019 |
| JP | 6980386 B2 | 11/2021 |
| WO | 94/21166 A1 | 9/1994 |
| WO | 9843530 A1 | 10/1998 |
| WO | 0168178 A1 | 9/2001 |
| WO | 2005114720 A2 | 12/2005 |
| WO | 2008091197 A1 | 7/2008 |
| WO | 2008157399 A1 | 12/2008 |
| WO | 2012145074 A1 | 10/2012 |

* cited by examiner

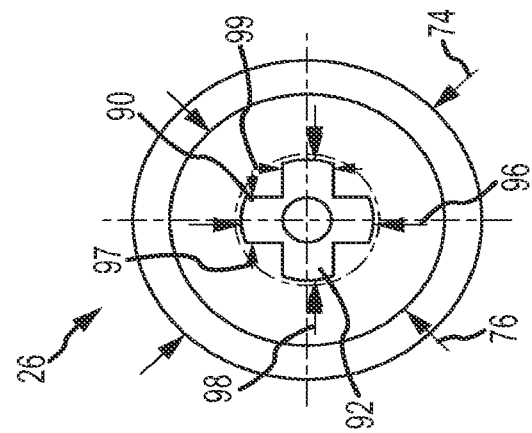
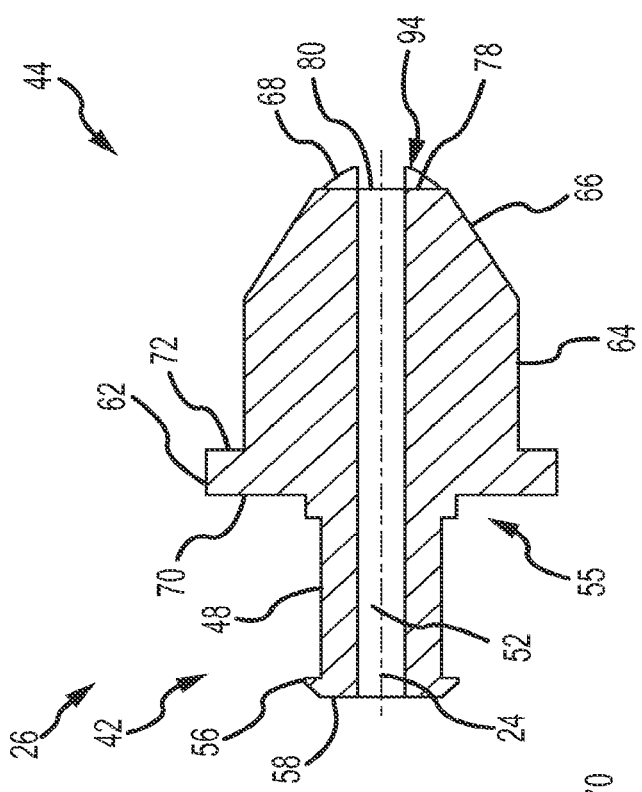
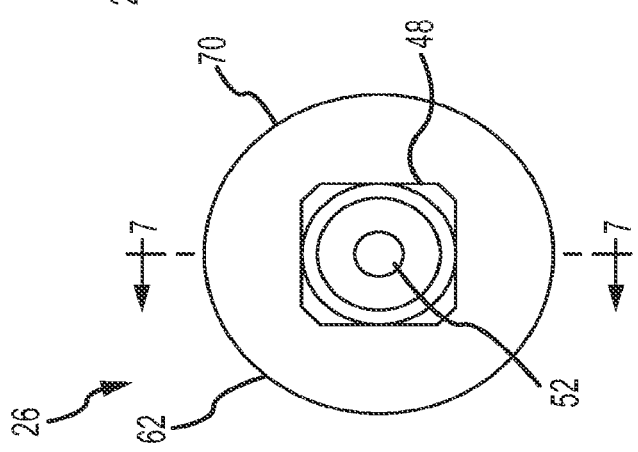

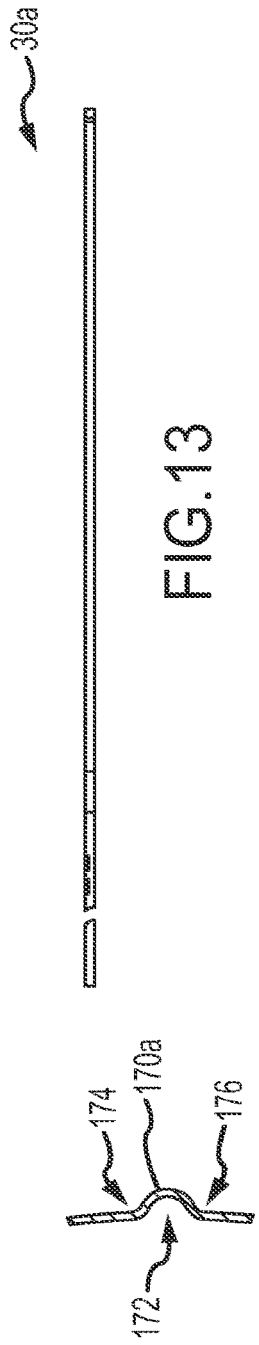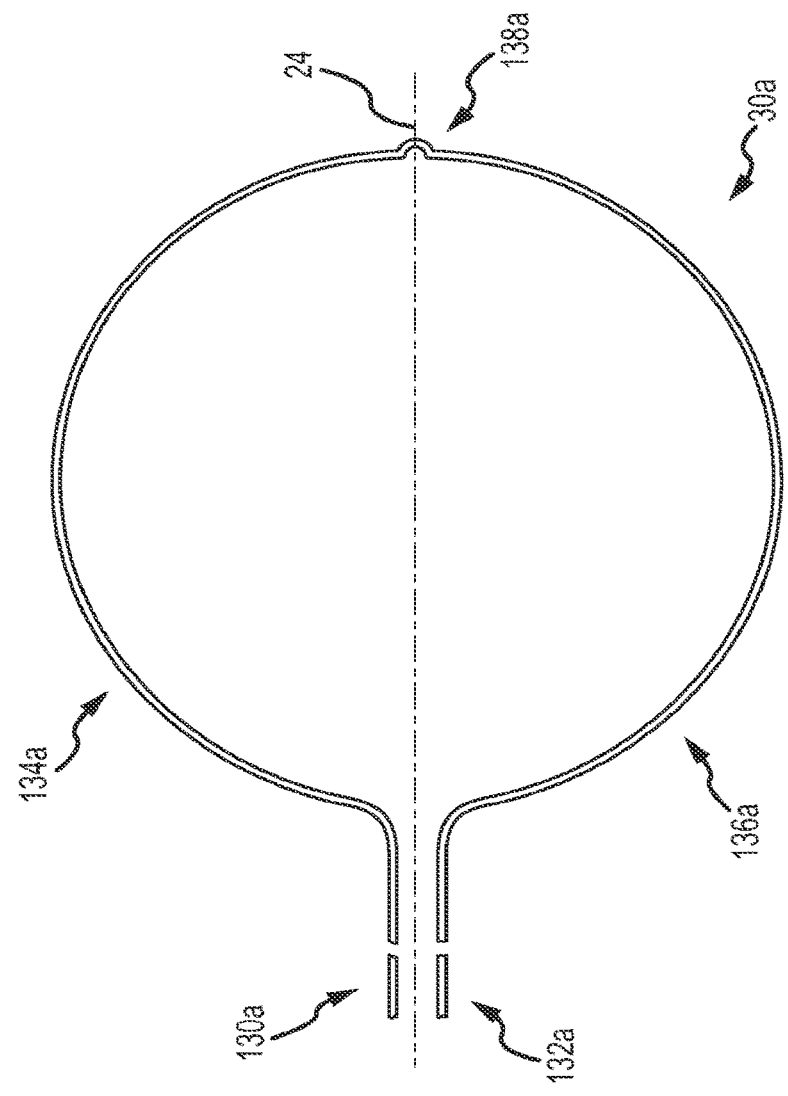

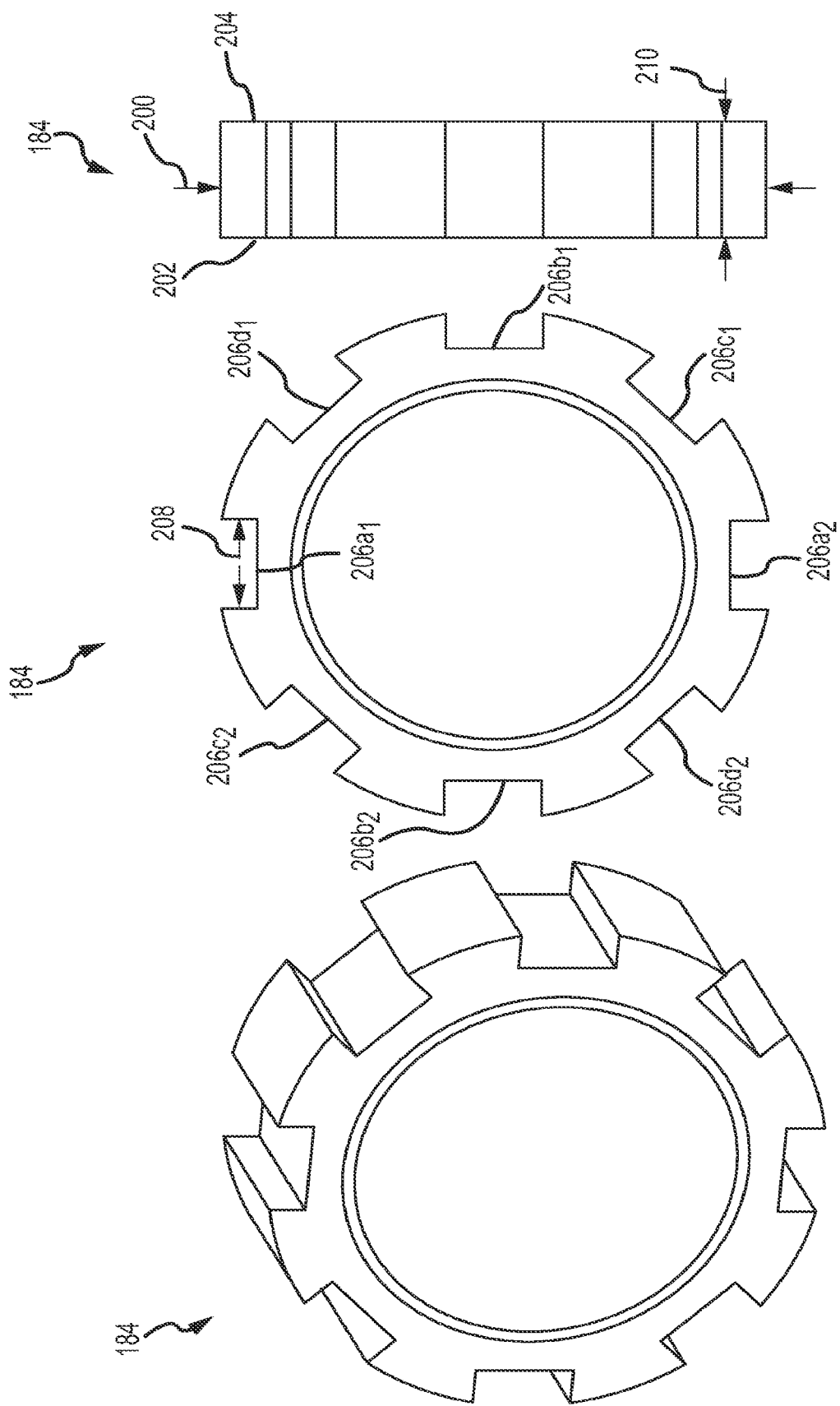

ELECTRODE SUPPORT STRUCTURE ASSEMBLY

BACKGROUND a. Technical Field

This disclosure relates generally to an electrode support structure assembly. In particular, the instant disclosure relates to an electrode support structure assembly for basket catheters including a plurality of arms.

b. Background Art

This background description is set forth below for the purpose of providing context only. Therefore, any aspects of this background description, to the extent that it does not otherwise qualify as prior art, is neither expressly nor impliedly admitted as prior art against the instant disclosure.

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart or a chamber or vein thereof. The catheter carries one or more electrodes that can be used for cardiac mapping or diagnosis, ablation and/or other therapy delivery modes, or both, for example. Once at the intended site, treatment can include, for example, radio frequency (RE) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

Various catheters and electrode arrangements can be employed for different purposes. Catheters having basket-shaped electrode support structures are generally described in, for example and without limitation, U.S. Pat. No. 5,772,590, the entire disclosure of which is incorporated herein by reference as though set forth in its entirety. Generally, catheters having basket-shaped electrode support structures are introduced through a guiding sheath with the electrode support structure in a folded or collapsed position within the sheath so that the electrode support structure does not damage tissue during its introduction. Once the catheter reaches its intended position within the heart, the guiding sheath can be removed and/or the catheter extended therefrom and the electrode support structure can be allowed to radially outwardly expand for cardiac mapping or diagnosis, ablation, and/or other therapy delivery modes, or both, for example.

Typically, basket-shaped electrode support structures comprise a plurality of arms that can be formed from laser-cut tubing and be integral at one end or that comprise discrete, separate elements. The distal ends of each of these plurality of aims generally must be joined together. For example, the distal ends of each of the plurality of arms can be mounted around a first piece of tubing and then be held in place by a second piece of tubing as generally described and illustrated in U.S. Pat. No. 7,522,950.

It may be desirable for each of the arms to be joined in such a way that the arms are configured to straighten evenly when the electrode support structure is collapsed. However, it may be difficult for the electrode support structure to collapse evenly if manufacturing variances have resulted in differences in the individual lengths of the arms. It may also be difficult for the electrode support structure to collapse evenly if one or more of the arms have experienced a change in length relative to the remainder of the arms, such as during manipulation of the electrode support structure around a curve, for example. If the arms do not straighten evenly when the electrode support structure is collapsed, a protrusion or "loop" can form at the distal end of one or more of the plurality of arms. Continued collapse or multiple collapses of the electrode support structure can potentially cause fatigue at the point of the protrusion or "loop" and ultimately fracture the arm. Moreover, when the distal ends of the arms are fixed in place (e.g., mounted between two pieces of tubing), the distal flexibility of the arms may be limited, thereby adversely impacting the collapsibility of the electrode support structure. In addition, stress imparted at the distal end of the electrode support structure during collapse and/or expansion of the electrode support structure can also result in the failure of any arm or other element that may be configured to join the distal ends of the aims together.

Additionally, when the electrode support structure is in an expanded state, electrode distribution may not be uniform in accordance with some electrode arrangements. Moreover, during expansion and/or collapse of the electrode support structure (e.g., when the electrode support structure is emerging from or being retracted into a delivery sheath), some electrode arrangements may possibly result in electrode-to-electrode physical contact and/or electrical short circuits, which may cause electrode wear and/or limit electrode functionality. In addition, some electrode arrangements may not minimize the profile of the electrode support structure during collapse of the electrode support structure, which can result in electrode damage when the electrode support structure is being delivered through the delivery sheath, especially when being delivered through a tortuously angulated pathway.

Basket-shaped electrode support structures can include an expander having a distal end attached to a distal end of the electrode support structure. The expander includes a proximal end that extends out of a proximal end of a catheter or other medical device employing the electrode support structure to a control handle. The expander can be moved longitudinally relative to the catheter or other medical device to expand and contract the electrode support structure. The expander is generally coaxial with the catheter. An expander will not generally allow for free axial movement of the electrode support structure if the electrode support structure is being diametrically constrained in some way.

Several difficulties may be encountered, however, during these medical procedures using some existing basket catheters. For example, a slowing or stoppage of the flow of blood may occur between the arms of the basket catheter, e.g., where the aims are attached to the catheter. Irrigation is desirable to keep fluid moving between the arms of the catheter.

There is therefore a need to minimize and/or eliminate one or inure of the problems as set forth above. The foregoing discussion is intended only to illustrate the present field and should not be taken as a disavowal of claim scope.

SUMMARY

Among other things, various embodiments disclosed herein are directed to an electrode support structure assembly.

An electrode support structure assembly in a body in accordance with one embodiment of the present teachings includes a plug, a cap, and a plurality of support members. The plug defines a longitudinal axis and is configured to connect to a fluid delivery line. The plug also includes a lumen configured to receive a fluid from the fluid delivery line, the lumen extending in an axial direction and comprising an axial distal end. The plug may further include a distal tip adjacent to the axial distal end of the lumen and comprising a first channel. The cap is disposed around at least a portion of the plug and includes a first wall extending in the axial direction and a plurality of apertures. The cap may further include a second wall extending inwardly from the first wall in a radial direction. The first wall and the second wall of the cap define an interior. Each support member of the plurality of support members comprises a distal portion. The distal tip of the plug and the distal portions of the plurality of support members are at least partially disposed in the interior of the cap. The cap is configured to constrain relative movement of the distal portions of the plurality of support members with respect to the cap, and the first channel of the plug and at least one of the plurality of support members are configured to direct a fluid after exiting the lumen of the plug.

An electrode support structure assembly with a longitudinal axis, a proximal portion, and a distal portion in accordance with another embodiment of the present teachings includes a support member, a constraining ring, a torsion ring, and a retainer ring. The support member includes a first proximal portion extending in the axial direction and a second proximal portion generally parallel to the first proximal portion. The constraining ring is disposed at the proximal portion of the assembly and is configured to constrain the first and second proximal portions of the support member in the axial direction. The torsion ring is disposed at the proximal portion of the assembly and is configured to constrain rotation of the first and second proximal portions of support member about the longitudinal axis. The retainer ring partially surrounds at least one of the constraining ring and torsion ring and is configured to secure the first and second proximal portions of the support member relative to at least one of the constraining ring and torsion ring.

It is desirable to provide an electrode support structure assembly that can include an element joining the distal end of each of the plurality of aims that is configured to provide freedom for each of the plurality of arms to move independently along an axis of the electrode support structure. This may help ensure that the arms are configured to straighten evenly when the electrode support structure is collapsed. It is also desirable to provide an electrode support structure assembly that can include an element joining the distal end of each of the plurality of arms that is configured to provide freedom for each of the plurality of arms to articulate relative to an axis of the electrode support structure such that each of the plurality of aims can be positioned at numerous angles relative to the axis of the electrode support structure in order to minimize stress imparted at the distal end of the electrode support structure during collapse and/or expansion. It is also desirable to provide an electrode support structure that can be configured to allow for free, uniform axial displacement even if the electrode support structure is being diametrically constrained in some way. It is also desirable to effectively deliver irrigation fluid to the distal end of the catheter while concurrently keeping the components of the catheter as small and compact as possible.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 6 is a rear elevational view of the plug illustrated in FIGS. 5A-5B.

FIG. 7 is a cross-sectional view of the plug of FIG. 6 taken along line 7-7.

FIG. 8 is a front elevational view of the plug illustrated in FIGS. 5A-5B.

FIG. 12 is a lateral elevational view of the support member of FIG. 11.

FIG. 13 is a top elevational view of the support member of FIG. 11.

FIG. 14 is a lateral view of a nose of the support member illustrated in FIG. 11.

FIG. 21 is an isometric view of a torsion ring of the proximal subassembly illustrated in FIG. 17.

FIG. 22 is a front devotional view of the torsion ring of FIG. 21.

FIG. 23 is a lateral elevational view of the torsion ring of FIG. 21.

DETAILED DESCRIPTION

Figure 1:
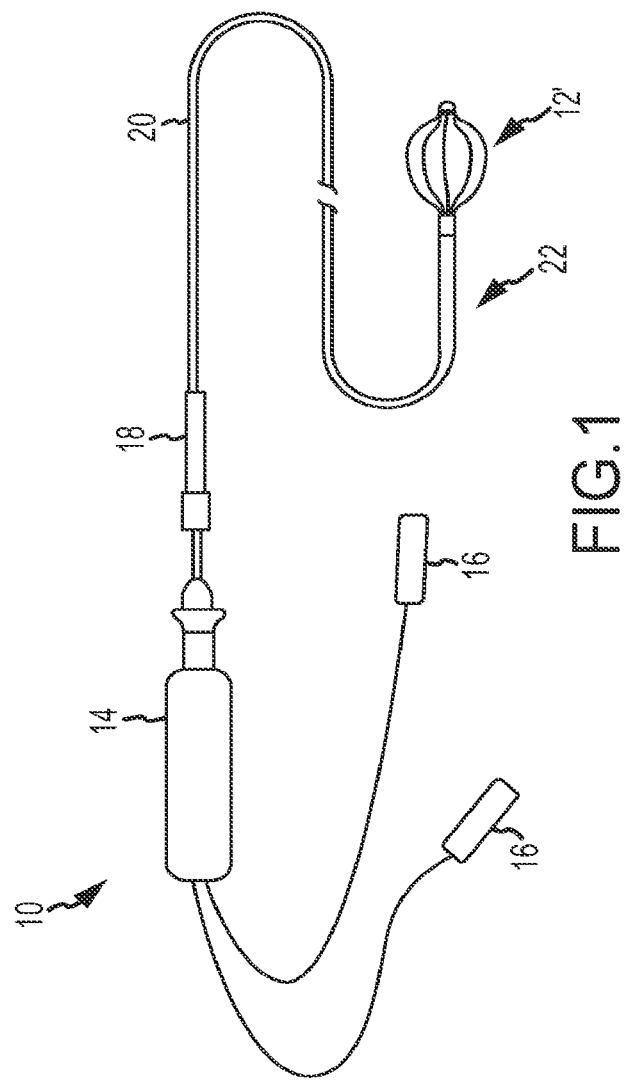
FIG. 1 is a diagrammatic view of a catheter system that is designed to perform one or more diagnostic and/or therapeutic functions in accordance with at least one embodiment of the present teachings.

It may be desirable to be able to deliver saline or an anticoagulant such as a heparinized saline solution or other fluid in a basket catheter during various medical procedures, e.g., to reduce the risk of blood clot or thrombus formation. One effective way to prevent blood coagulation and thrombus formation is to irrigate the electrode with heparinized saline. It is still further desirable to be able to do all of this while retaining the ability to axially move a deployment mechanism, e.g., a basket catheter, or electrode support structure itself. Moreover, designing components of the electrode support structure assembly to fit tightly together (so as to keep the catheter footprint as small as possible) can interfere with the desire to provide unconstrained delivery of irrigation fluid.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of a medical device or instrument used to treat a patient. The term "proximal" refers to the portion of the device closest to the clinician (or to a robotic control configured to manipulate the device) and the term "distal" refers to the portion located furthest from the clinician. It will be further appreciated that for conciseness and clarity, spatial terms such as "vertical," "horizontal," "up," and "down" may be used herein with respect to the illustrated embodiments. However, medical devices may be used in many orientations and positions, and these terms are not intended to be limiting or absolute. Moreover, as used herein, the term "basket" is not limited to the illustrated configuration, but can include other designs such as spherical or egg-shaped designs, for example.

Referring now to the drawings wherein like reference numerals are used to identify identical or similar components in the various views, FIG. 1 is a diagrammatic view of a catheter system 10 employing an electrode assembly 12' in accordance with an embodiment of the present teachings. Catheter system 10 includes a handle 14 and connectors 16 disposed proximal to handle 14 for making electrical connections to a visualization, navigation, and/or mapping system (not shown) such as those systems available under the brand name Ensite™ NaVX™ (aka Ensite™ "Classic" as well as newer versions of the Ensite™ system, denoted as Ensite™ Velocity™) and available from St. Jude Medical, Inc. Handle 14 can have a uni-directional design, a bi-directional design, or any other suitable design and be accordingly configured to steer electrode assembly 12', as discussed in more detail in commonly assigned U.S. Pat. No. 8,676,290, the entire disclosure of which is incorporated herein by reference. Catheter system 10 can also include an introducer 18 located distally of handle 14 that may be used to deliver an elongated catheter body 20 into the body of a patient, through a hemostasis valve of another longer introducer, for example, Elongated catheter body 20 can extend from introducer 18. Elongated catheter body 20 can comprise an elongated tubular construction having one or more lumens. Elongated catheter body 20 can be flexible or bendable. Elongated catheter body 20 can be of any suitable construction and made of any suitable material as known to those of ordinary skill in the art, Elongated catheter body 20 can have any outer diameter, but may generally be configured for insertion into the vascalature of a body of a patient and, in some embodiments, be less than about 8 French. Elongated catheter body 20 can have an outer wall of any thickness, but may generally be configured so that one or more lumens can be disposed within elongated catheter body 20 to accommodate pull wires, lead wires, sensor cables, and any other wires, cable, and/or tubes that may be needed in particular applications. Handle 14, connectors 16, introducer 18, and elongated catheter body 20 can be readily modified as dictated by the aesthetic or functional needs of particular applications.

Electrode assembly 12' is configured to extend from a distal portion 22 of elongated catheter body 20. Although electrode assembly 12' is described and illustrated in connection with an intracardiac catheter system 10, electrode assembly 12' may be utilized in connection with other types of medical devices, such as for example and without limitation, stone retrieval baskets, distal protection devices, renal artery ablation devices, snares, and other retrieval devices. As discussed in further detail below in connection with FIGS. 3-4, assembly 12' may be configured to support electrodes and to be radially outwardly expandable and inwardly collapsible.

Figure 2:
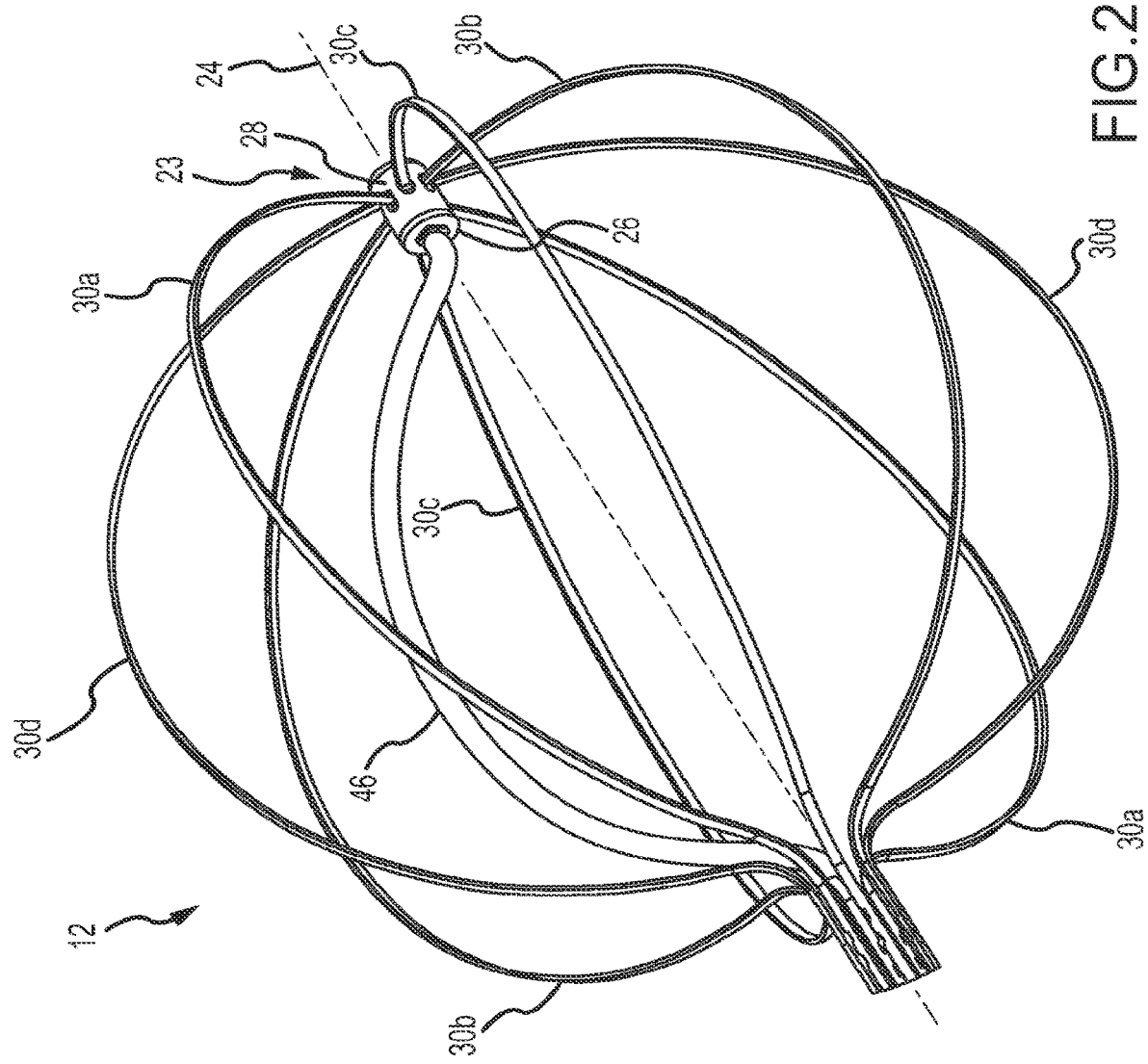
FIG. 2 is an isometric view of an electrode support structure assembly in accordance with one embodiment of the present teachings.

FIG. 2 is an isometric view of an electrode support structure assembly 12. Assembly 12 is configured to be mounted to distal portion 22 of elongated catheter body 20. Assembly 12 is configured to be radially outwardly expandable relative to axis 24 to an expanded arrangement as shown in FIG. 2. Assembly 12 defines a longitudinal axis 24 and may be configured to be radially inwardly collapsible relative to axis 24 to a collapsed arrangement. Assembly 12 may comprise a distal subassembly 23 which may include a plug 26 and a cap 28 disposed around a portion of plug 26. Assembly may further include support members 30a-d. Support members 30a-d of assembly 12 can be collapsed by an application of force, for example, by moving support members 30a-d into a sheath or introducer. Upon removal of the application force, for example, by moving support members 30a-d out of a sheath or introducer, support members 30a-d may return to the expanded arrangement. This expansion and collapse of assembly 12 may alternatively or additionally be achieved by using a shape memory material for support members 30a-d in accordance with some embodiments. The expansion and collapse of assembly 12 may be achieved by using a biasing mechanism in accordance with other embodiments. In the illustrated embodiment, assembly 12 may include four support members 30a-d. Although four support members 30a-d are mentioned in detail, there may be fewer or more support members in accordance with various embodiments. Each of the support members 30a-d may generally be evenly spaced circumferentially around axis 24 of the assembly 12. Assembly 12 may further include a proximal subassembly 32 (best shown in FIG. 17) to be described in more detail hereinbelow. Moreover, support members 30a-d may be generally circular in shape and may each have two free ends connected to proximal subassembly 32 with distal subassembly 23 being disposed at the opposite end (see FIG. 11).

Still referring to FIG. 2, catheter system 10 may further include a fluid delivery line 46 in accordance with some embodiments Fluid delivery line 46 may be connected to an irrigation system and include, for example and without limitation, an irrigation pump configured to supply irrigation fluid to assembly 12 and/or distal portion 22 of catheter body 20 (shown in FIG. 1). In an embodiment, when assembly 12 is expanded (as illustrated in FIG. 2), fluid delivery line 46 may be generally arc-shaped between proximal subassembly 32 (FIG. 3) and distal subassembly 23. When collapsed, fluid delivery line 46 is generally straight and lies along longitudinal axis 24. Such a configuration allows fluid delivery line 46 to be free of any undue tension while assembly 12 is being collapsed (e.g., into a guiding sheath). In one embodiment, the arc length of fluid delivery line 46 is approximately the same (or slightly less than) the arc length of support members 30a-d between proximal subassembly 32 (FIG. 3) and distal subassembly 23. One of ordinary skill in the art will understand that fluid delivery line 46 may take on a number of other configurations, For example and without limitation, fluid delivery 46 may be generally straight when collapsed and expanded by being corrugated, functioning similarly as a spring.

Figure 3:
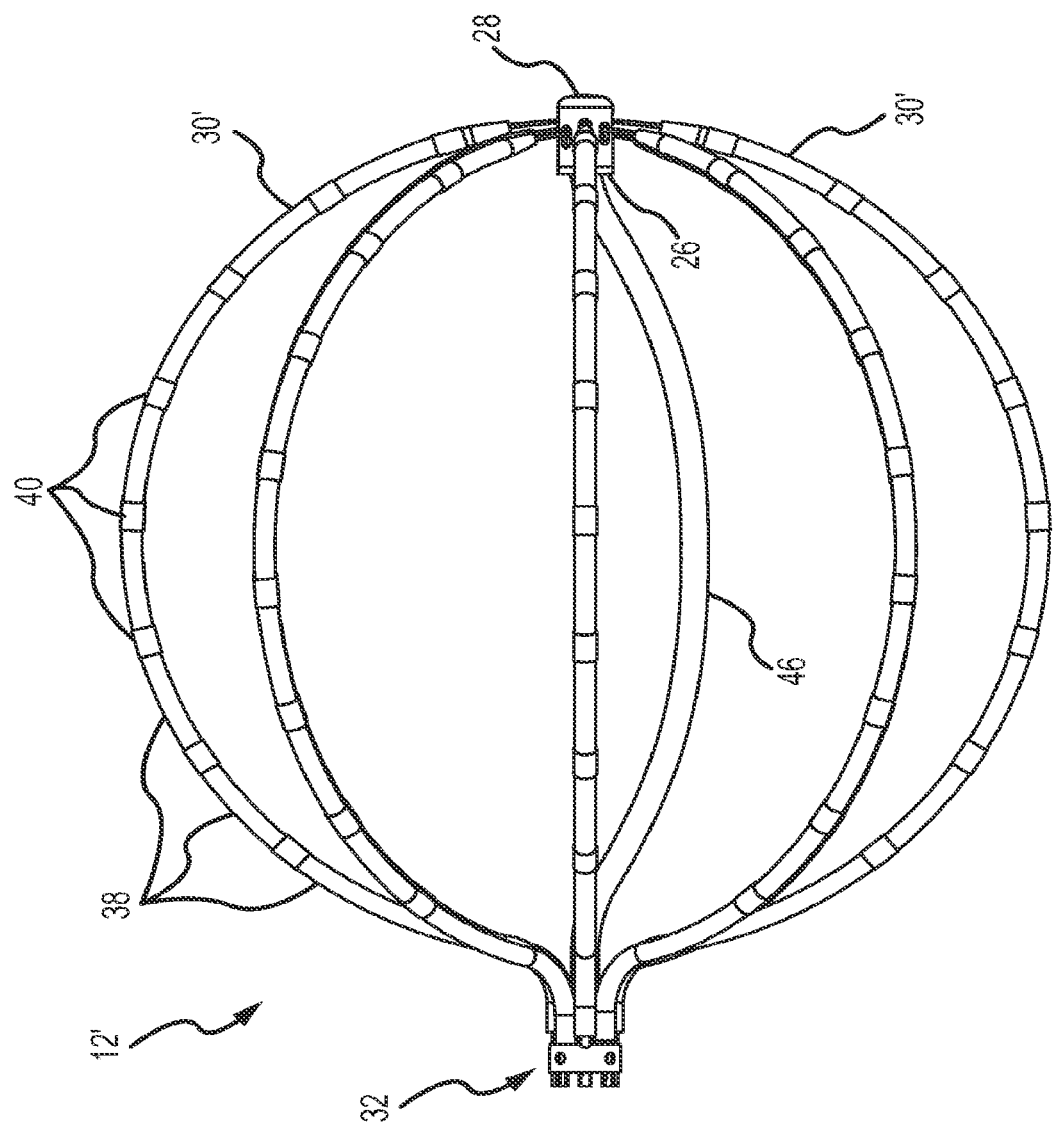
FIG. 3 is a lateral elevational view of an electrode assembly in accordance with another embodiment of the present teachings.
Figure 4:
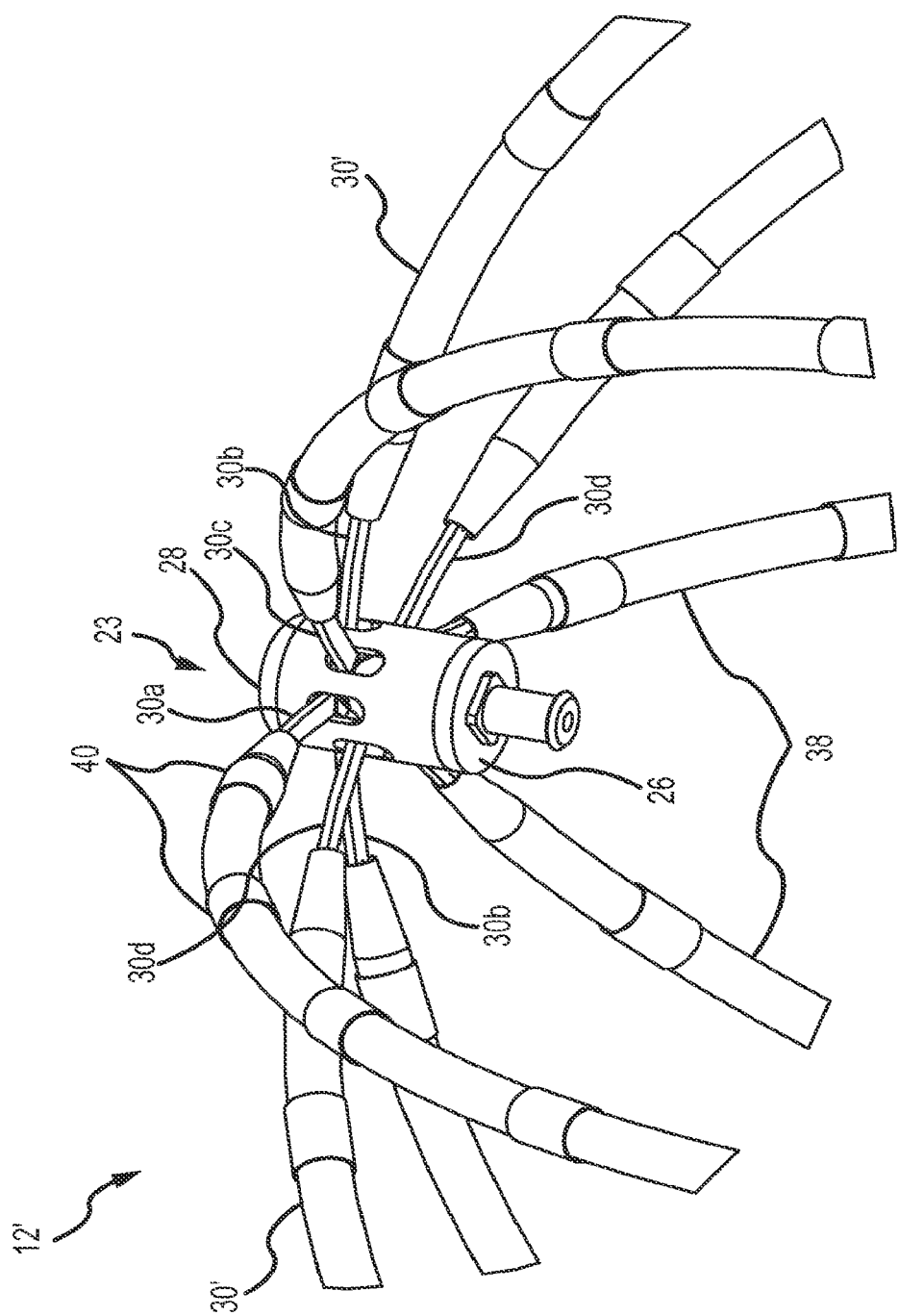
FIG. 4 is an isometric view of a portion of the electrode assembly illustrated in FIG. 3.

FIGS. 3-4 generally illustrate electrode assembly 12' (shown generally in FIG. 1). Assembly 12' is similar to assembly 12 of FIG. 2 except that assembly 12' includes additional components. Fluid delivery line 46 has been omitted in FIG. 4 for clarity. In the illustrated embodiment shown in FIGS. 3-4, assembly 12' comprises arms 30', with each aim 30' comprising a support member 30a-d, a nonconductive covering 38 surrounding each support member 30a-d, and electrodes 40. In accordance with some embodiments, support members 30a-d may each be a flexible wire and may be fiat and/or composed of Nitinol or other like materials. The non-conductive covering 38 can comprise a biocompatible plastic tubing, such as polyurethane or polyimide tubing in accordance with some embodiments. Although these materials are mentioned in detail, support members 30a-d and covering 38 can be made of any other suitable materials known to those of ordinary skill in the art. For example and without limitation, the arms 30' can be designed without support members 30a-d if a sufficiently rigid non-conductive material is used. One or more of the arms 30' can have one or more electrodes 40 mounted on the non-conductive covering 38 in accordance with various embodiments. The number and spacing of electrodes 40 on the arms 30' can vary in accordance with various embodiments. The material and configuration. of arms 30' (and/or support members 30a-d) can vary, as generally shown and discussed in U.S. Pat. No. 8,588,885, the entire disclosure of which is incorporated herein by reference. Individual components of electrode support structure assembly 12 (FIG. 2) will now be discussed in detail. A discussion of how the components interact and couple together will follow.

Figure 5A:
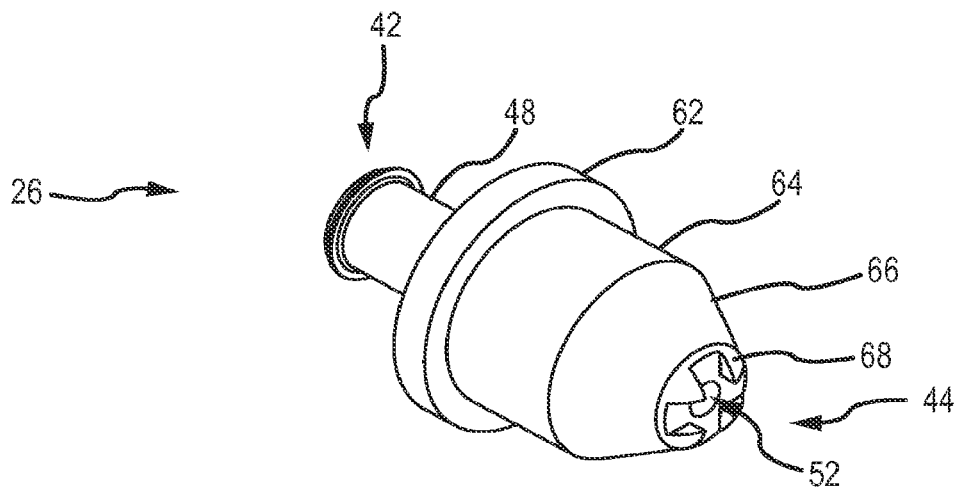
FIGS. 5A-5B are isometric views of a plug of the electrode support structure assembly illustrated in FIG. 2.
Figure 5B:
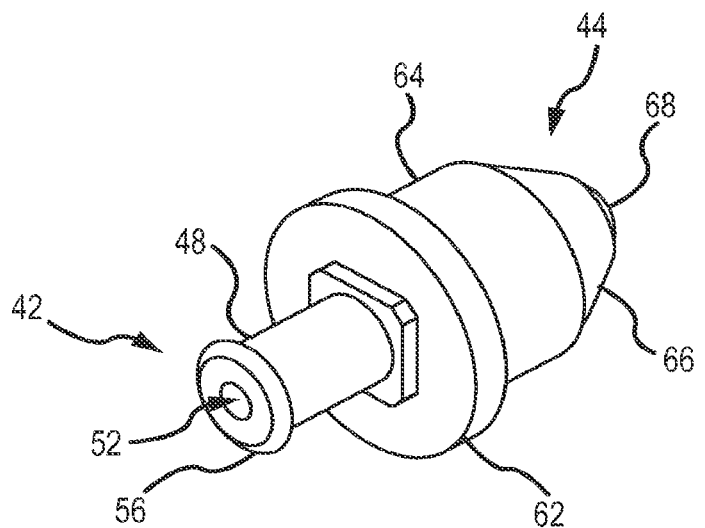

FIGS. 5A-8 illustrate various views of plug 26 of electrode support structure assembly 12 shown in FIG. 2. Referring to FIGS. 5A-5B, plug 26 has a proximal portion 42 and a distal portion 44. At its proximal portion 42, plug 26 comprises a connector portion 48 configured to connect to fluid delivery line 46 (connection best seen in FIG. 26). In one embodiment, connector portion 48 may be generally cylindrical about longitudinal axis 24 and include a barb 56 and a proximal end 58. Barb 56 is configured to secure fluid delivery line 46 in place. In an embodiment, an adhesive may also be used to secure fluid delivery line 46 in place. At its distal portion 44 (and as explained in more detail below), plug 26 is configured to control the directional flow of the fluid when assembled with other components described herein. In the illustrated embodiment, plug 26 further includes a lumen 52 generally disposed along longitudinal axis 24 extending between proximal portion 42 and distal portion 44 (lumen 52 and longitudinal axis 24 best seen in FIG. 7).

Figure 26:
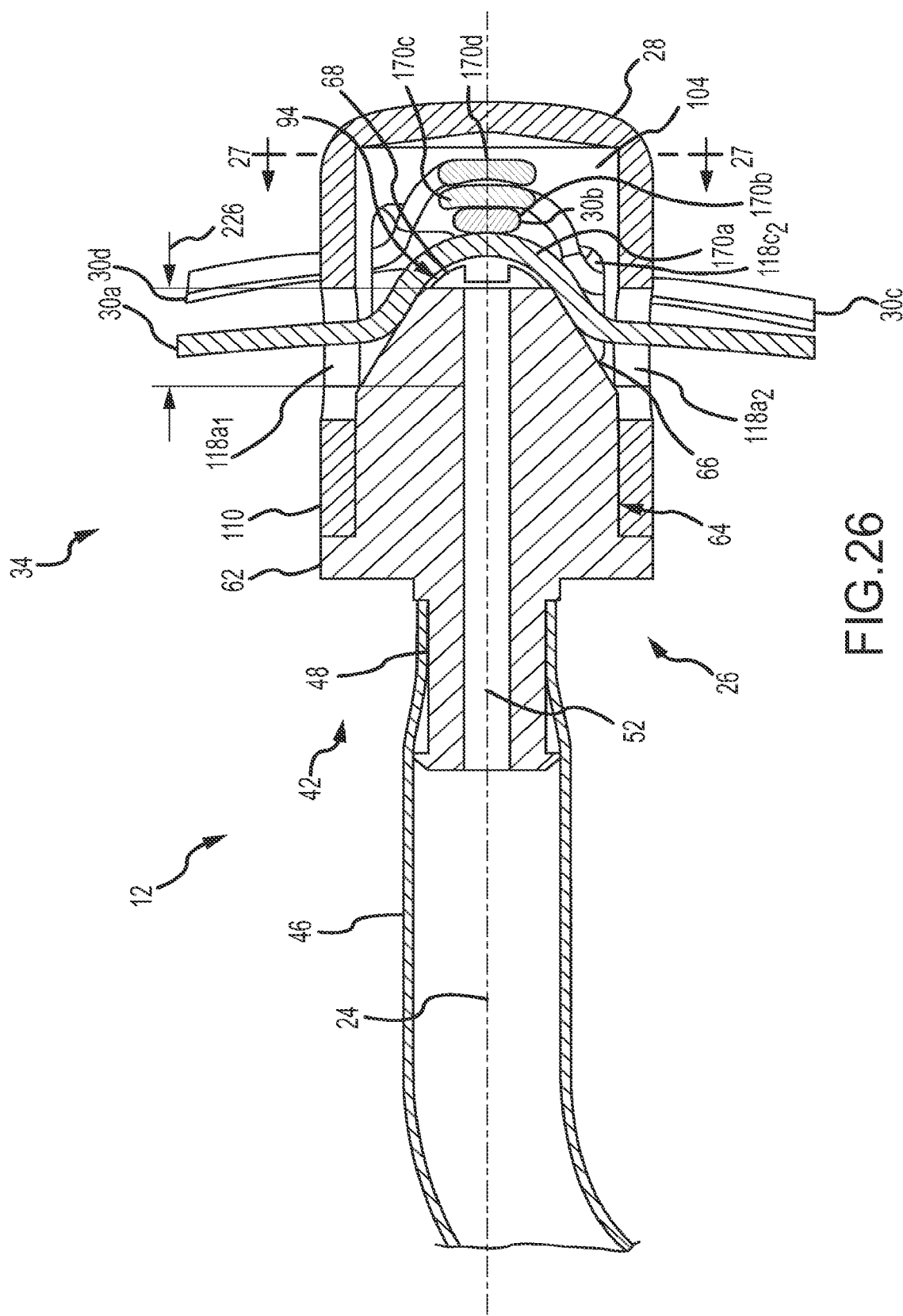
FIG. 26 is a cross-sectional view of a portion of the electrode support structure assembly of FIG. 2 taken along line 26-26 in FIG. 27.

In one embodiment, plug 26 is configured to couple with cap 28 of assembly 12 (coupling of elements 26, 28 best shown in FIG. 26). Referring to FIG. 5A, in one embodiment, plug 26 includes a ring portion 62, a cylindrical portion 64 distal of ring portion 62, a tapered portion 66 distal of cylindrical portion 64, and a distal tip 68. Referring to FIG. 7, in the illustrated embodiment, ring portion 62 has a proximal face 70, a distal face 72, and an outer diameter 74 (as best seen in FIG. 8) and abuts connector portion 48 at its proximal face 70. Cylindrical portion 64 may have an outer diameter 76 (as best seen in FIG. 8), which (in one embodiment) is smaller than outer diameter 74 of ring portion 62. Tapered portion 64 may extend distally from cylindrical portion 64 to distal tip 68 and may have a distal end 78. Moreover, tapered portion 64 may be tapered in the axial direction toward an axial distal end 80 of lumen 52. In the illustrated embodiment, distal tip 68 is adjacent to axial distal end 80 of lumen 52 and includes channels 90, 92 (as best seen in FIG. 8) and is rounded with a radius of curvature 94 (as best seen in FIG. 7).

Channels 90, 92 are configured to direct the fluid outwardly in a radial direction (relative to longitudinal axis 24) after exiting lumen 52 (when assembled with other components described herein). In the illustrated embodiment (and as best seen in FIG. 8), channels 90, 92 may each extend across distal tip 68 and longitudinal axis 24 with channel 90 being oriented vertically and channel 92 being oriented horizontally. As such, channels 90, 92 may intersect. Channels 90, 92 may each have a length 96, 98 and a width 97, 99 in accordance with some embodiments. As illustrated, channels 90, 92 generally have semi-rectangular cross sections. One of ordinary skill in the art will appreciate that channels 90, 92 can have a number of different cross sections (such as semi-circular or semi-triangular), and each can have a different cross section. Moreover, each channel 90, 92 may have varying cross sections across its length 96, 98. Additionally, in accordance with other embodiments, distal tip 68 may have one or more than two channels, with the channel(s) extending in various radial directions. For example and without limitation, distal tip 68 may have four channels, each equidistant from the adjacent channels about longitudinal axis 24. It should be understood that channels 90, 92 may not be equidistant about longitudinal axis 24. In the illustrated embodiment, channels 90, 92 are disposed distally of axial distal end 80 of lumen 52 (FIG. 7); channel 90 is perpendicular to longitudinal axis 24 and channel 92; and channel 92 is perpendicular to longitudinal axis 24 and channel 90. In accordance with other embodiments, however, channels 90, 92 extend at an angle(s) less than or greater than 90 degrees from longitudinal axis 24 and/or from each other.

Referring particularly to FIG. 7, lumen 52 is generally configured to direct the fluid from proximal portion 42 of plug 26 to distal portion 44 of plug 26. In an embodiment, lumen 52 lies along longitudinal axis 24 and extends from proximal end 58 of connector portion 48 to distal end 78 of tapered portion 66. In the illustrated embodiment, axial distal end 80 of lumen 52 corresponds with distal end 78 of tapered portion 66. Although lumen 52 is illustrated as having a round cross section (best shown in FIGS. 6 and 8), one of ordinary skill in the art will appreciate that lumen 52 can have a number of different cross sections. Moreover, plug 26 may include more than one lumen extending parallel or at an angle to longitudinal axis 24 (or another lumen) in accordance with other embodiments.

Figure 9:
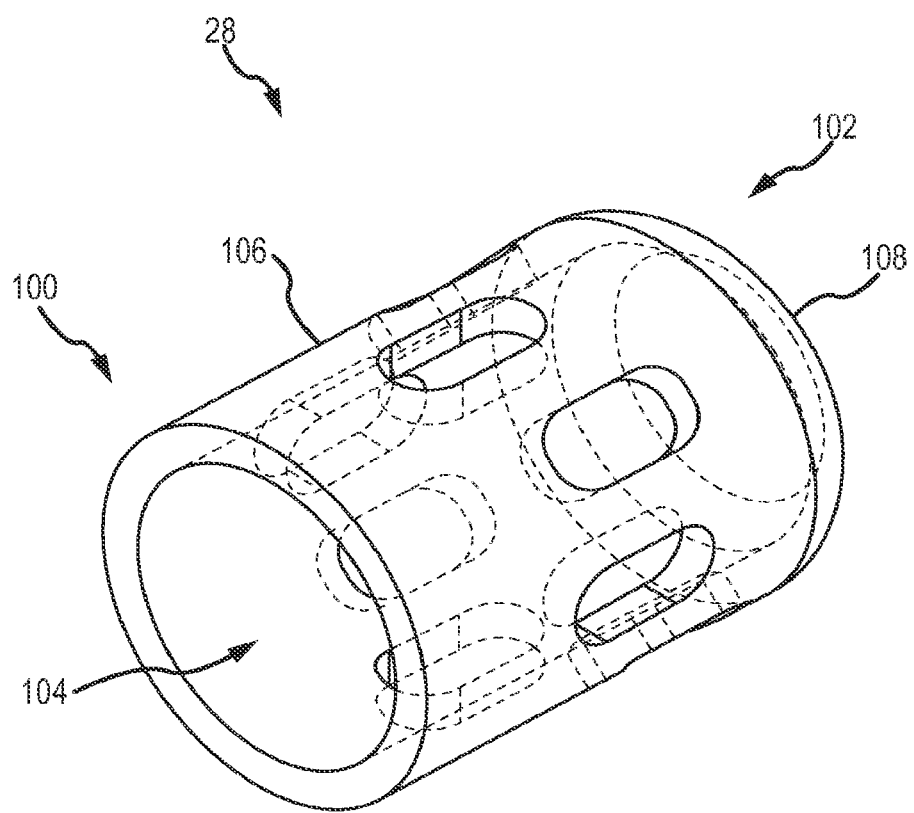
FIG. 9 is an isometric view of a cap of the electrode support structure assembly illustrated in FIG. 2.
Figure 10:
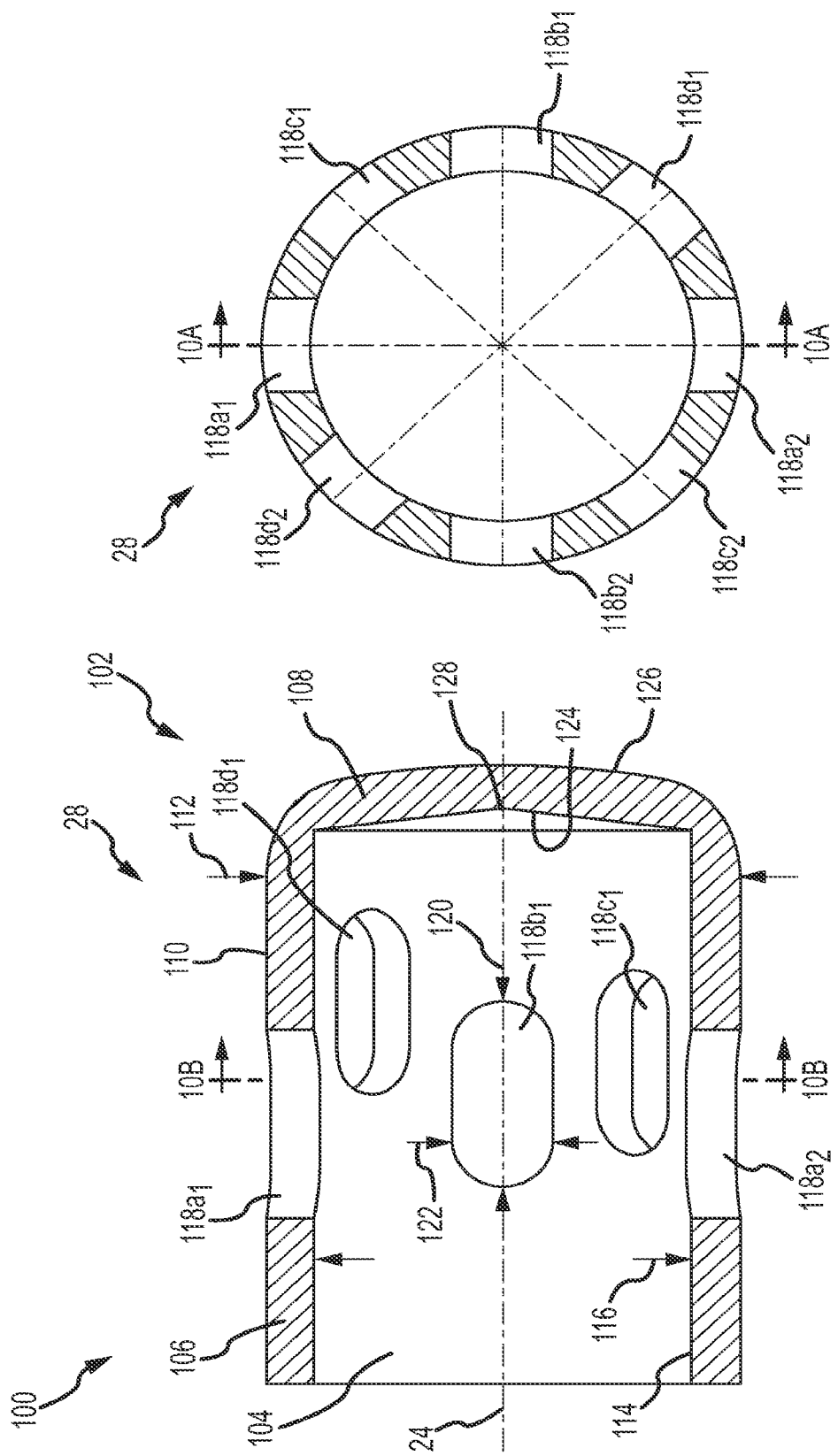
FIG. 10A is a cross-sectional view of the cap of FIG. 9 taken along line 10A-10A in FIG. 10B.
FIG. 10B is a cross-sectional view of the cap of FIG. 9 taken along line 10B-10B in FIG. 10A.

FIGS. 9-10B generally illustrate various views of cap 28 of the electrode support structure assembly 12 shown in FIG. 2. Referring to FIG. 9, cap 28 is generally cylindrical in shape and has a proximal portion 100, a distal portion 102, and an interior 104 and is configured to be coupled with plug 26 (coupling discussed in more detail below). In other, embodiments, however, cap 28 may take on other shapes, such as rectangular or octagonal. Cap 28 is also configured to constrain movement of support members 30a-d.

Referring to FIG. 10A, in the illustrated embodiment, cap 28 is generally disposed along longitudinal axis 24 and has a circumferential wall 106 extending in the axial direction along longitudinal axis 24 and an axial end wall 108 at distal portion 102 extending inwardly from circumferential wall 106 in the radial direction. In an embodiment, circumferential wall 106 and axial end wall 108 define interior 104. Circumferential wall 106 may have an outer surface 110 with an outer diameter 112, an inner surface 114 with an inner diameter 116, and apertures $118a_1$-$d_2$ through which support members 30a-d may extend. Apertures $118a_1$-$d_2$ may be configured to permit the fluid to exit interior 104. Referring to FIG. 10B, in the illustrated embodiment, circumferential wall 106 has four pairs of apertures $118a_1$-$d_2$ each pair corresponding to an individual support member 30a-d (as can best be seen in FIG. 27). The two apertures (e.g., $118a_1$, $118a_2$) in each pair are diametrically opposed of one another about longitudinal axis 24 in accordance with an embodiment. One of ordinary skill in the art will understand that circumferential wall 106 may have less than or more than eight apertures in accordance with other embodiments. Referring to FIG. 10A, apertures $118a_1$-$d_2$ may have a length 120 and a width 122. In the illustrated embodiment, apertures $118a_1$-$d_2$ are generally the same size and shape; however, in other embodiments, the apertures may have different sizes and shapes. In the illustrated embodiment, each aperture $118a_1$-$d_2$ is generally rectangular in shape with rounded corners and has substantially the same size and shape at outer surface 112 and at inner surface 114. However, it should be understood that each aperture may have a different size and/or shape at inner surface 114 and outer surface 112. In an embodiment, each pair of apertures $118a_1$-$d_2$ may be offset a distance from the proximally adjacent pair of apertures 118a-d in the axial direction. For example and without limitation, as best seen in FIG. 10A, apertures $118a_1$, $118a_2$ may be disposed most proximally in the axial direction, followed by apertures $118b_1$, $118b_2$, then apertures $118c_1$, $118c_2$, and lastly, apertures $118d_1$, $118d_2$. One of ordinary skill in the art will appreciate that apertures 118a-d may be disposed in a number of ways relative to each other and that the sequential offset order may be varied. Moreover, apertures $118a_1$-$d_2$ may not be offset from one another and, instead, lie in the same radial planes along longitudinal axis 24 (i.e., apertures $118a_1$-$d_2$ may be substantially aligned in the axial direction). Axial end wall 108 may have an inner surface 124 and an outer surface 126. Outer surface 126 of axial end wall 108 may extend from outer surface 110 of circumferential wall 106, and inner surface 124 of axial end wall 108 may extend from inner surface 114 of circumferential wall 106, in accordance with some embodiments. In an embodiment, inner surface 124 of axial end wall 108 has an apex 128 located on longitudinal axis 24 and is generally conical in shape, It should be understood, however, that inner surface 124 can take on a number of profiles or shapes, For example and without limitation, inner surface 124 may be flat or rounded. Outer surface 126 of axial end wall 108 may be rounded in accordance with one embodiment.

FIGS. 11-16 generally illustrate various views of support member 30a of electrode support structure assembly 12 shown in FIG. 2. Although only support member 30a is illustrated in FIGS. 11-16, support members 30b-d are identical to support member 30a in the illustrated embodiment. Having support members 30a-d be identical makes fabrication of assembly 12 more cost-effective. However, it should be understood that support members 30a-d do not have to be identical in size and shape in accordance with other embodiments.

Figure 11:
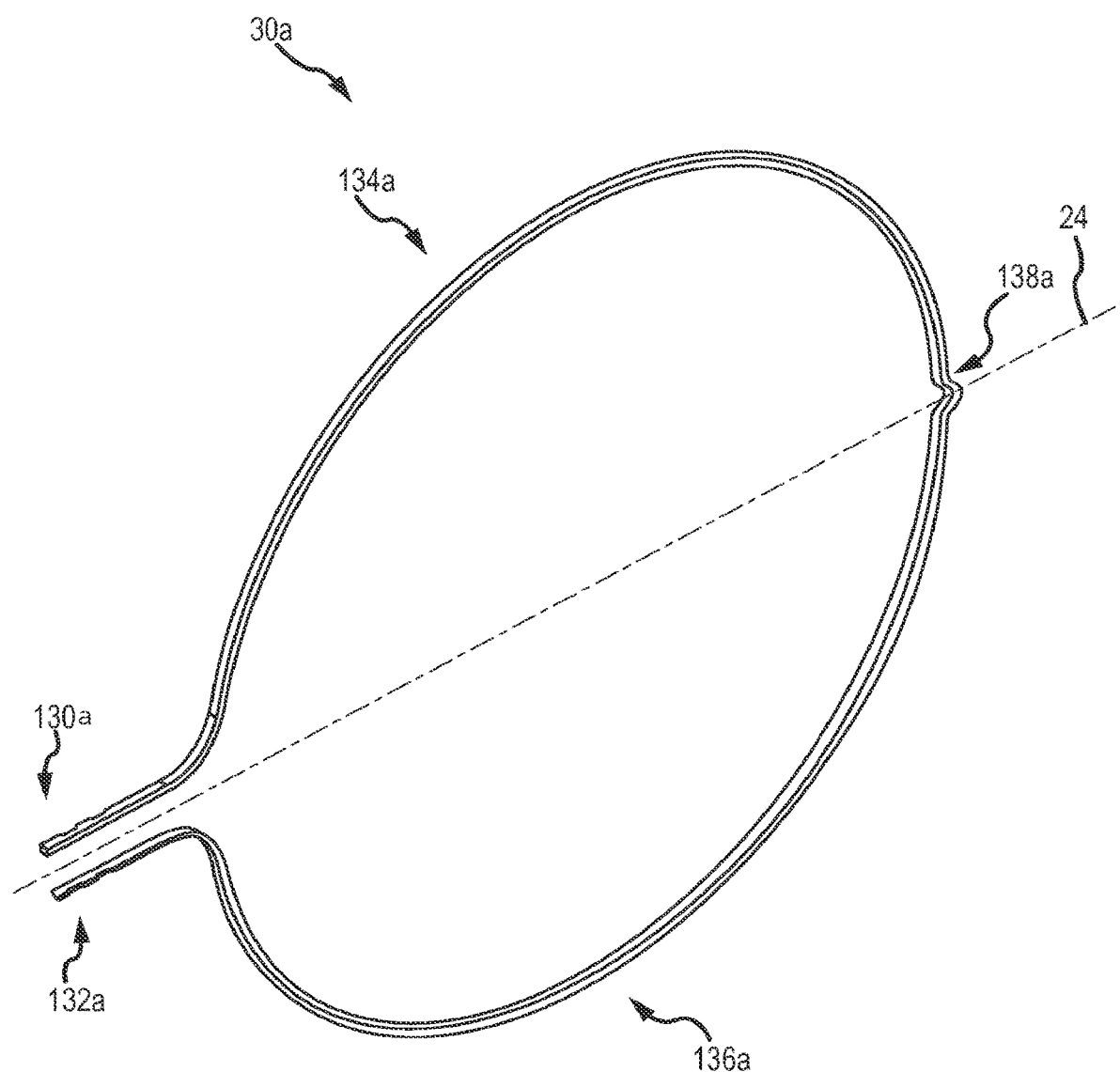
FIG. 11 is an isometric view of a support member of the electrode support structure assembly illustrated in FIG. 2.

FIG. 11 is an isometric view of support member 30a illustrated in FIG. 2. Support members 30a-d are deflectable and configured to assume different configurations during operation. For example and without limitation, electrode support structure assembly 12 (once assembled) can comprise a "basket" in which each of the support members 30a-d can splay or bow radially outwardly (as best seen in FIG. 2). The particular shape of the "basket" can vary. For example and without limitation, one or more of the support members 30a-d can splay or bow radially outwardly and uniformly (relative to each other) along the length of assembly 12, away from longitudinal axis 24, or one or more of the support members 30a-d can splay or bow radially outwardly in varying amounts along the length of assembly 12. The resulting "basket" is generally symmetric about the longitudinal axis 24 of assembly 12 in accordance with some embodiments. Although a "basket" shape is mentioned in detail, support members 30a-d can assume any number of other shapes in accordance with. various embodiments. Although first and caps 26, 28 and support members 30a-d extend along longitudinal axis 24, they may have their own individual longitudinal axis, with each axis being parallel or at angle to one another.

Support member 30a may have proximal portions 130a, 132a, intermediate portions 134a, 136a, and a distal portion 138a. Although in the illustrated embodiment support member 30a is one continuous generally circular piece, one of ordinary skill in the art will understand that support member 30a can be any number of distinct pieces. For example, and without limitation, support member 30a may be cut at distal portion 138a to form two generally semi-circular members. in one embodiment, proximal portions 130a, 132a are generally parallel to each other and longitudinal axis 24 of assembly 12.

Figure 15:
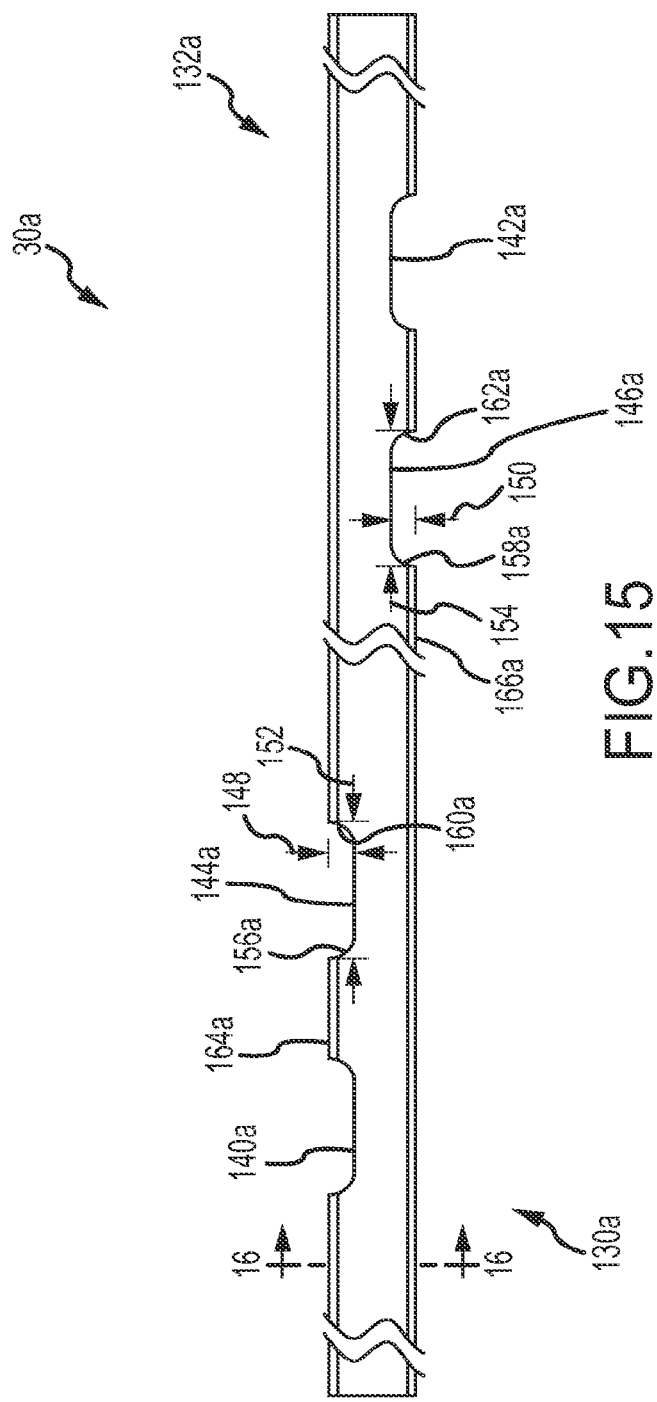
FIG. 15 is a plan view of proximal portions of the support member of FIG. 11 prior to formation.

FIG. 15 is a plan view of proximal portions 130a, 132a of support member 30a of FIG. 11 prior to formation (as if support member 30a were laid out straight and unbent). Proximal portions 130a-d, 132a-d of each support member 30a-d (proximal portions 130a, 132a of support member 30a shown in FIG. 15) are configured to be coupled together, as will be described in more detail herein below in connection with FIGS. 17-24, and to distal portion 22 of catheter body 20 (shown in FIG. 1). Still referring to FIG. 15, proximal portions 130a, 132a each include an indicator slot 140a, 142a and a constraining slot 144a, 146a. After forming support member 30a into a generally circular shape (as shown in FIG. 11), indicator slots 140a, 142a are generally diametrically opposed of one another, and constraining slots 144a, 146a are generally diametrically opposed of one another as well. In an embodiment, indicator slots 140a, 142a serve as a visual aid in fabricating assembly 12. For example and without limitation, indicator slots 140a, 142a may indicate the location at which to cut support member 30a before, during, or after assembly. As will be described in more detail herein below in connection with FIGS. 18-20, constraining slots 144a, 146a are configured to secure proximal portions 132a, 134a of support member 30a in the axial direction and may each have a width 148, 150, a length 152, 154, and inner edges 156a, 158a, 160a, 162a, each inner edge extending in the radial direction. Although inner edges 156a, 158a, 160a, 162a are illustrated as being generally perpendicular relative to longitudinal axis 24, one of ordinary skill in the art will understand that edges 156a, 158a, 160a, 162a may extend at various angles relative to longitudinal axis It Support member 30a further includes sides 164a, 166a (shown in FIG. 16). In one embodiment, indicator slot 140a and constraining slot 144a of proximal portion 130a are disposed on side 164a and may face a first radial direction, and indicator slot 142a and constraining slot 146a of proximal portion 132a are disposed on side 166a and may face a second radial direction that is generally 180 degrees from the first radial direction (about axis 24). In the illustrated embodiment, each slot 140a, 142a, 144a, 146a has rounded corners. In other embodiments, the corners may not be rounded.

Figure 16:
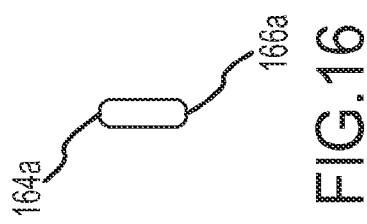
FIG. 16 is a cross-sectional view of the proximal portion of the support member of FIG. 15 taken along line 16-16.

Referring now to FIG. 16, in an embodiment, support member 30a has a generally roc cross section with rounded corners. In accordance with some embodiments, support member 30a generally has the same cross-sectional shape throughout its length. However, it should be understood that support member 30a may have varying cross sections in different places throughout its length. In the illustrated embodiment, support member 30a has substantially the same width throughout its length. However, it should be understood that support member 30a may have varying widths (and other dimensions) throughout proximal portions 130a, 132a, intermediate portions 134, 136a, and/or distal portion 138a.

Referring back now to FIGS. 12-14, in the illustrated embodiment, intermediate portions 134a, 136a of support member 30a extend from proximal portions 130a, 132a, respectively, and connect to distal portion 138a. 1n an embodiment (and as described in more detail herein above), intermediate portions 134a, 136a are configured to support electrodes 40. Distal portion 138a is configured to couple to intermediate portions 134a, 136a and includes a nose 170a protruding in the axial direction and extending radially inwardly from intermediate portions 134a, 136a toward longitudinal axis 24 and having a radius of curvature 172 (as best seen in FIG. 14), Nose 170a may also have radii of curvature 174, 176 where it connects to intermediate portions 134a, 136a. Although nose 170a is illustrated as being rounded, nose 170a may take on a variety of shapes and/or curvatures in accordance with other embodiments. Nose 170a may be configured and/or shaped to constrain movement thereof in interior 104 of cap 28 (as best illustrated in FIG. 26). Moreover, nose 170a may correspond in shape to at least one of tapered portion 66 and distal tip 68 of plug 26 (FIG. 26).

Figure 17:
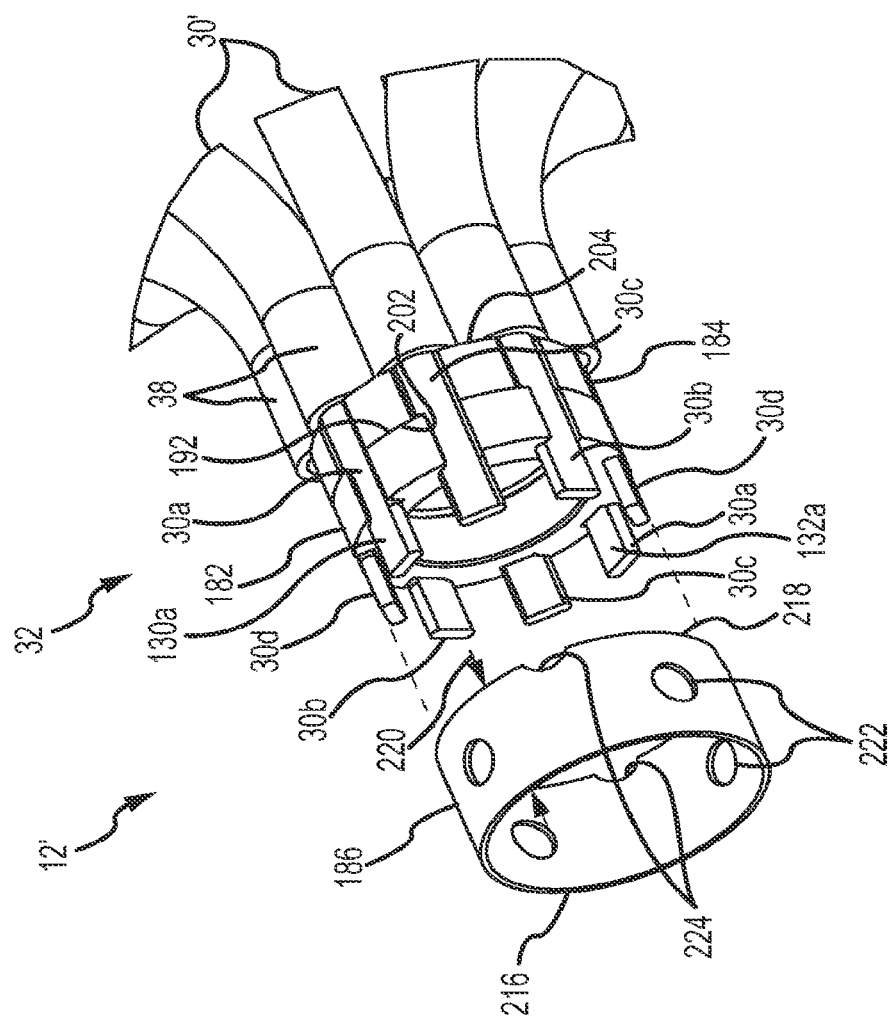
FIG. 17 is a partially exploded view of a proximal subassembly of the electrode assembly illustrated in FIG. 3.
Figure 20:
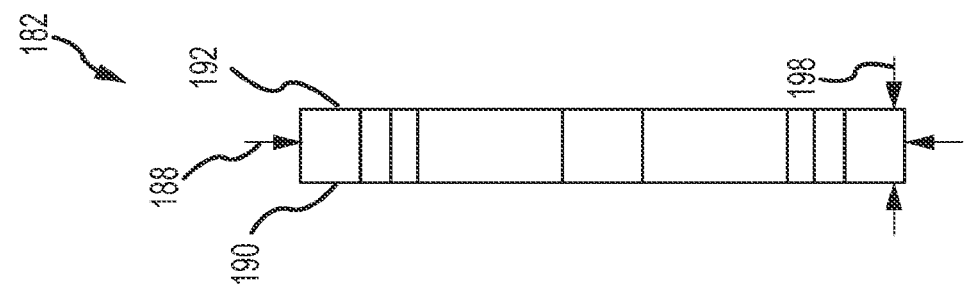
FIG. 20 is a lateral elevational view of the constraining ring of FIG. 18.
Figure 19:
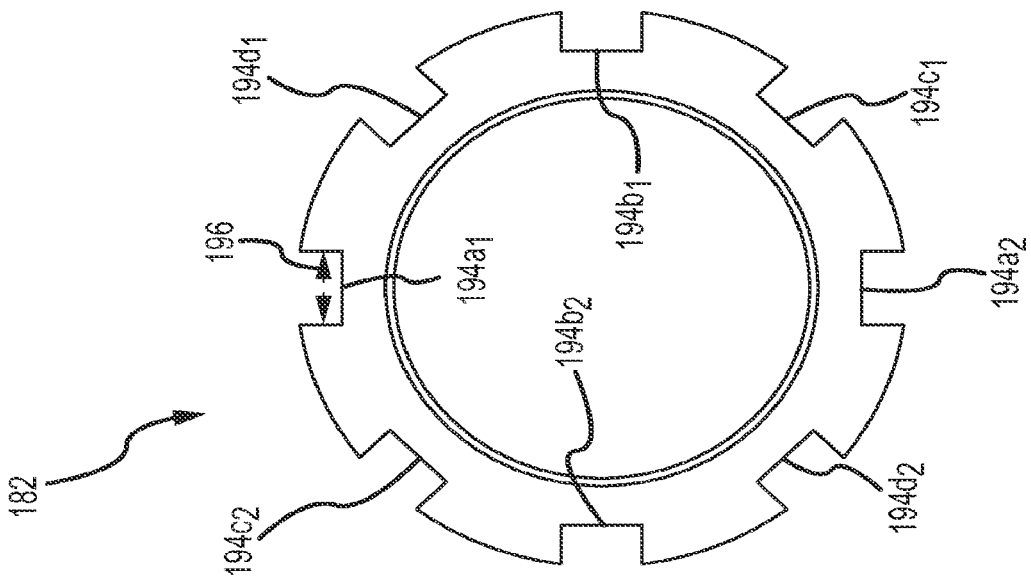
FIG. 19 is a front elevational view of the constraining ring of FIG. 18.
Figure 18:
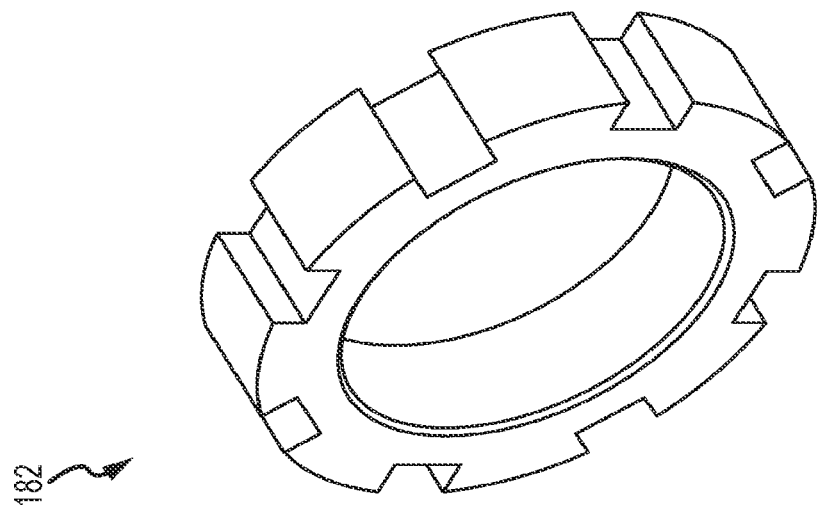
FIG. 18 is an isometric view of a constraining ring of the proximal subassembly illustrated in FIG. 17.

FIGS. 17-25 generally illustrate the coupling of arms 30' to proximal subassembly 32 and the components used therewith in accordance with one embodiment of the present teachings. FIG. 17 is a partially exploded view of proximal subassembly 32 illustrated in FIG. 3. Proximal subassembly 32 may include a constraining ring 182, a torsion ring 184, and a retainer ring 186. FIGS. 18-20 generally illustrate various views of constraining ring 182. In the illustrated embodiment, constraining ring 182 and torsion ring 184 have the same general shape except for the width of the grooves contained therein (to be described in more detail herein below). Constraining ring 182 is configured to couple with support members 30a-d (via constraining slots 144a-d, 146a-d in support members 30a-d, as shown in FIG. 15 with respect to support member 30a) and constrain movement of proximal portions 130a-d, 132a-d of support members 30a-d (as seen in FIGS. 11-12 with respect to support member 30a) in the axial direction, However, because support members 30a-d are flexible, other portions of support members 30a-d may move in the axial direction, namely intermediate portions 134, 136 and distal portion 138 (as shown in FIGS. 11-12).

Referring particularly to FIG. 20, in the illustrated embodiment, constraining ring 182 has an outer diameter 188 and includes a proximal face 190, a distal face 192, and eight grooves $194a_1$-$d_2$, each groove $194a_1$-$d_2$ having a width 196 and a length 198. In the illustrated embodiment, constraining ring 182 is configured to support one proximal portion 130a-d or 132a-d of one support member 30a-d. For example and without limitation, grooves $194a_1$, $194a_2$ (being diametrically opposed of one another) are configured to support proximal portions 130a, 132a of support member 30a, respectively. Likewise, grooves $194b_1$, $194b_2$ may support proximal portions 130b, 132b of support member 30b, respectively; grooves $194c_1$, $194c_2$ may support proximal portions 130c, 132c of support member 30c, respectively; and grooves $194d_1$, $194d_2$ may support proximal portions 130d, 132d of support member 30d, respectively. In FIG. 17, for clarity only proximal portions 130a, 132a of support member 30a are labeled if illustrated, the other support members 30b-d would include similar labels ending with the letters "b", "c", and "d", as appropriate. In some embodiments, the number of grooves $194a_1$-$d_2$ in the constraining ring 182 may correspond to the number of proximal portions 130a-d, 132a-d of support members 30a-d. Because in the illustrated embodiment, there arc four support members 30a-d, each with two proximal portions 130a-d, 132a-d, there are eight grooves $194a_1$-$d_2$ in constraining ring 182. One of ordinary skill in the art would understand, however, that the number of grooves in constraining ring may vary and may not necessarily correlate to the number of support members and/or proximal portions of support members. Moreover, in accordance with other embodiments, not every proximal portion 130a-d, 132a-d of support members 30a-d may be secured within constraining ring 182. In the illustrated embodiment, support members 30a-d are identical parts; therefore, constraining slots 144a-d, 146a-d (constraining slots 144a, 146a. shown in FIG. 15) all lie in the same relative position along the length of support members 30a-d. It should be understood, however, that the position of constraining slots 144a-d, 146a-d may vary. For example and without limitation, constraining slots 144a, 146a on support member 30a may be offset from constraining slots 144d, 146d on support member 30d to compensate for the axial displacement of noses 170a-d (due to the stacking of noses 170a-d in the axial direction, as will be discussed in more detail below in connection with FIGS. 26-27).

In the illustrated embodiment (and as best seen in FIG. 15), edges 156a, 158a of slots 144a, 146a of support member 30a contact proximal face 190 of constraining ring 182, and edges 160a, 162a of slots 144a, 146a of support member 30a contact distal face 192 of constraining ring 182. This configuration constrains movement of proximal portions 130a, 132a of support member 30a in the axial direction. Width 196 of grooves $194a_1$-$d_2$ and the width of the portion of support members 30a-d disposed within grooves $194a_1$-$d_2$ may be designed accordingly. For example and without limitation, width 196 of grooves $194a_1$-$d_2$ may be 0.0115 inches, and the width of the portion of support members 30a-d disposed within grooves $194a_1$-$d_2$ may be 0.010 inches. Moreover, length 198 of grooves $194a_1$-$d_2$ and length 152, 154 of slots 144a-d, 146a-d of support members 30a-d may be designed accordingly. For example and without limitation, length 198 of grooves $194a_1$-$d_2$ may be 0.020 inches, and length 152, 154 of slots 144a-d, 146a-d of each support member 30a-d may be 0.024 inches.

Referring now to FIGS. 21-23, torsion ring 184 may be disposed distally of constraining ring 182 and may be configured to couple with proximal portions 130a-d, 132a-d of support members 30a-d and constrain rotation of proximal portions 130a-d, 132a-d support members 30a-d about longitudinal axis 24. However, because support members 30a-d are flexible, other portions of support members 30a-d may twist slightly in the rotational direction, namely intermediate portions 134a-d, 136a-d and distal portions 138a-d. In the illustrated embodiment, torsion ring 184 has an outer diameter 200 and includes a proximal face 202, a distal face 204, and eight grooves $206a_1$-$d_2$, each groove $206a_1$-$d_2$ having a width 208 and a length 210 and is configured to support one proximal portion 130a-d or 132a-d of support member 30a-d. For example and without limitation, grooves $206a_1$, $206a_2$ (being diametrically opposed of one another) are configured to support proximal portion 130a and proximal portion 132a of support member 30a, respectively. Likewise, grooves $206b_1$, $206b_2$ may support proximal portions 130b, 132b of support member 30b, respectively; grooves $206c_1$, $206c_2$ may support proximal portions 130c, 132c of support member 30c, respectively; and grooves $206d_1$, $206d_2$ may support proximal portions 130d, 132d of support member 30d, respectively. The number of grooves $206a_1$-$d_2$ in torsion ring 184 may correspond to the number of proximal portions 130a-d, 132a-d of support members 30a-d. Because in the illustrated embodiment, there are four support members 30a-d each with two proximal portions 130a-d, 132a-d, there are eight grooves $206a_1$-$d_2$ in torsion ring 184. One of ordinary skill in the art will understand, however, that the number of grooves in the torsion ring may vary and may not necessarily correlate to the number of support members and/or proximal portions of support members. Moreover, in accordance with other embodiments, not every proximal portion 130a-d, 132a-d of support members 30a-d may be secured within torsion ring 184.

In the illustrated embodiment, proximal face 202 of torsion ring 184 abuts distal face 192 of constraining ring 182 in the axial direction (as best seen in FIG. 17). However, in accordance with other embodiments, torsion ring 184 may not abut constraining ring 182 and/or be disposed proximally of constraining ring 182. Moreover, constraining ring 182 and torsion ring 184 may be constructed to be one piece rather than two separate rings. One of ordinary skill in the art would understand that not all rings 182, 184, 186 may be necessary. In the illustrated embodiment, edges 164a-d, 166a-d of proximal portions 130a-d, 132a-d of support members 30a-d (edges 164a, 166a shown in FIG. 16) are disposed within grooves $206a_1$-$d_2$ to constrain rotation about longitudinal axis 24. Width 208 of grooves $206a_1$-$d_2$ and width of the portion of support members 30a-d disposed within grooves $206a_1$-$d_2$ may be designed accordingly. For example and without limitation, width 208 of grooves $206a_1$-$d_2$ may be 0.0155 inches, and the width of the portion of support members 30a-d disposed within grooves $206a_1$-$d_2$ may be 0.014 inches.

Figure 24:
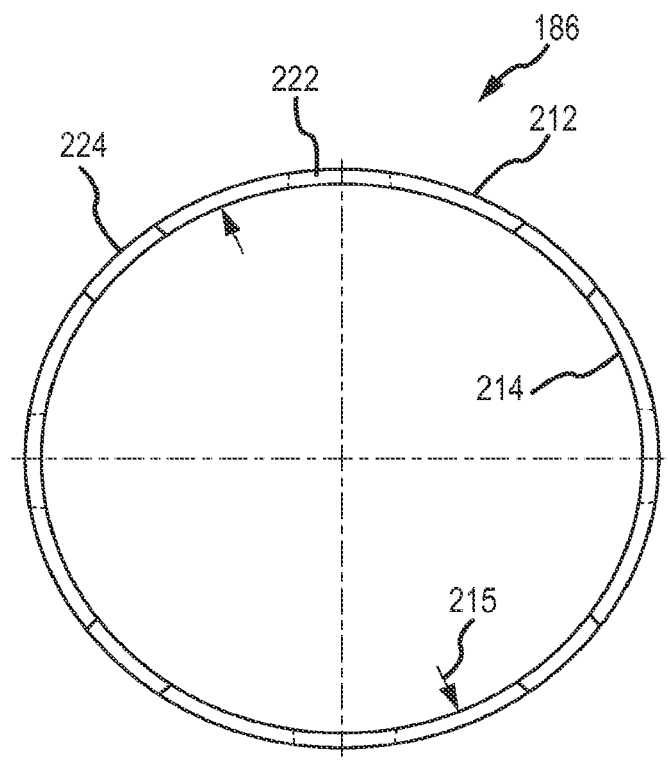
FIG. 24 is a front elevational view of a retainer ring of the proximal subassembly of FIG. 17.

Referring now to FIGS. 17 and 24 (with fluid delivery line 46 removed in FIG. 17 for clarity), retainer ring 186 may be disposed around constraining ring 184 and torsion ring 182 and may be configured to secure proximal portions 130a-d, 132a-d of support members 30a-d relative to at least one of constraining ring 184 and torsion ring 182. As shown in FIG. 24, retainer ring 186 may include an outer surface 212, an inner surface 214, and an inner diameter 215. As shown in FIG. 17, retainer ring 186 may further include a proximal face 216, a distal face 218, a width 220, and apertures 222, 224. Inner surface 214 is configured to contact proximal portions 130a-d, 132a-d of support members 30a-d and/or constraining ring 182 and torsion ring 184. For example and without limitation, inner diameter 215 of retainer ring 186 may be 0.092 inches, and outer diameter 188 of constraining ring 182 and outer diameter 200 of torsion ring 184 may be 0.0875 inches in accordance with one embodiment (diameters 188, 200 shown in FIGS. 20 and 23, respectively). Apertures 222, 224 may be configured to be filled with epoxy or adhesive to allow for greater bond strength. In the illustrated embodiment, there are eight apertures 222, 224: four apertures 222 are circular and are disposed centrally along width 220 in the axial direction, and four apertures 224 are semi-circular and are disposed along distal face 218. However, one of ordinary skill in the art would understand that there may be more or less apertures with various shapes and sizes. Moreover, width 220 of retainer ring 186 may be 0.040 inches, and widths 196, 208 of constraining ring 182 and torsion ring 184 (seen in FIGS. 19 and 22, respectively) may be 0.020 inches each. As best seen in FIG. 17, in the illustrated embodiment, support members 30a-d are coupled to/within rings 182, 184, 186 with non-conductive coating 38 abutting distal faces 204, 218 of torsion ring and retainer ring, respectively.

Figure 25:
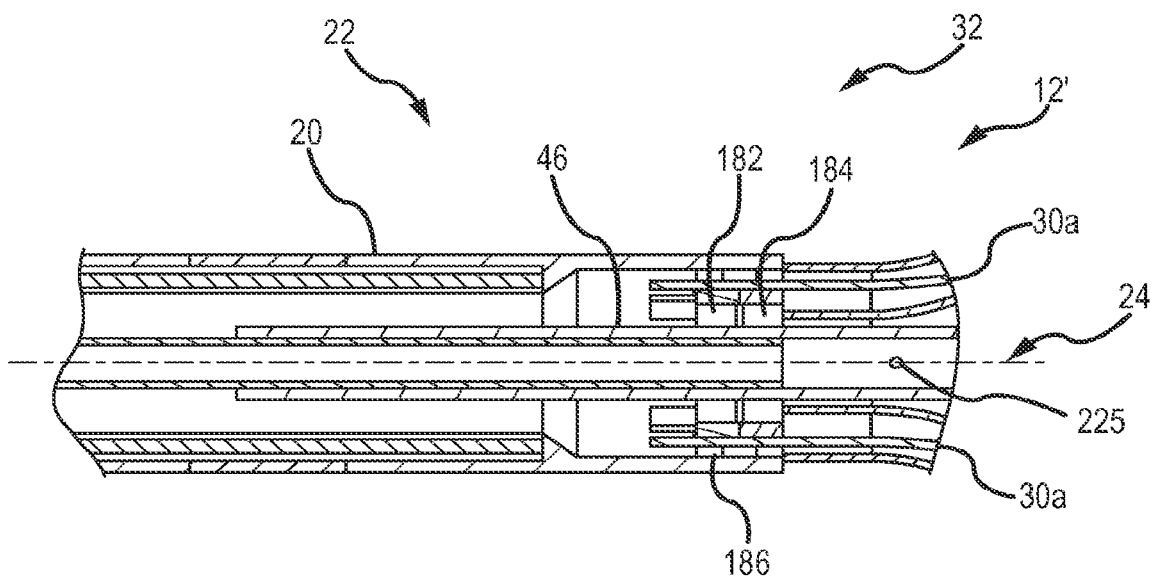
FIG. 25 is a cross-sectional view of the connection between an elongated catheter body and the electrode assembly of FIG. 3.

FIG. 25 is a cross-sectional view of the connection between elongated. catheter body 20 and assembly 12' of FIG. 3. In an embodiment, fluid delivery line 46 may extend along longitudinal axis 24. In an embodiment, fluid delivery line 46 may include at least one port, such as port 225. Port 225 may allow fluid to exit fluid delivery line 46 and may be located near proximal subassembly 32 outside of catheter body 20. One of ordinary skill in the art would understand that port 225 may be located at any point along longitudinal axis 24 outside catheter body 20. Moreover, although the catheter system 10 in the illustrated. embodiments allows for irrigation near proximal subassembly 32 via port 225 and distal subassembly 23 (as shown in FIG. 2) via apertures $118a_1$-$d_2$, catheter system 10 may only allow for irrigation at one subassembly 32, 23 and/or at a point(s) therebetween. Moreover, in another embodiment, fluid delivery line 46 may include three ports that are spaced 120 degrees apart about longitudinal axis 24 and are in the same longitudinal position along axis 24. In other embodiments, there may be any number of ports, and they may lie in various positions along and about longitudinal axis 24. Furthermore, the ports may be the same or different sizes and configurations other than circular (as illustrated).

Figure 27:
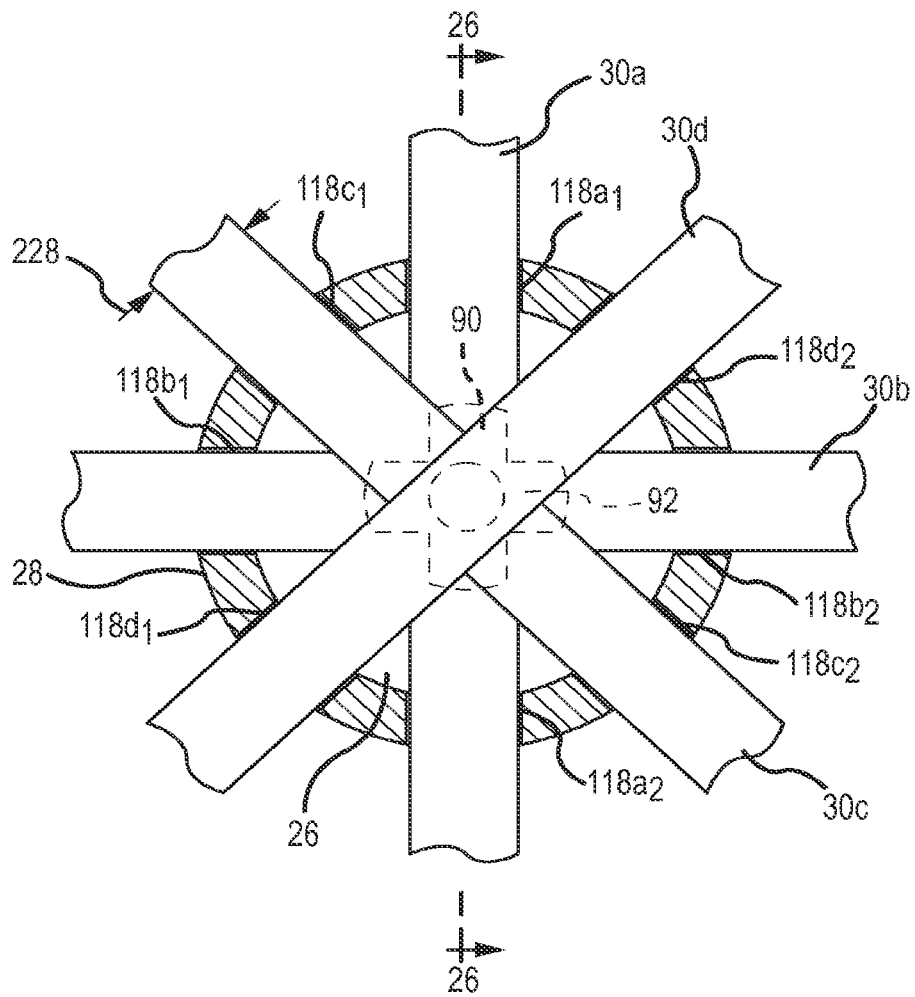
FIG. 27 is a cross-sectional view of the portion of the electrode support structure assembly of FIG. 26 taken along line 27-27.

FIGS. 26-27 generally illustrate a portion of the electrode support structure assembly 12 of FIG. 2 at distal subassembly 23, Referring particularly to FIG. 26, as illustrated, fluid delivery line 46 is connected to connector portion 48 of plug 26 such that fluid enters lumen 52 at proximal portion 42 of plug 26 and travels toward distal tip 68. In an embodiment, cap 28 is laser-welded to plug 26 at ring portion 62 of plug 26. For example and without limitation, cap 28 can be laser-welded to plug 26 in four different areas along ring portion 62 where it contacts cap 28. In another embodiment, cap 28 can be laser-welded to plug 26 along cylindrical portion 64 where it contacts cap 28. In yet another embodiment, plug 26 and cap 28 can be coupled together using screws. Screws may extend through ring portion 62 into circumferential wall 110 of cap 28 and/or through circumferential wall 110 of cap 28 into cylindrical portion 64 of plug 26. One of ordinary skill in the art will understand that plug 26 and cap 28 may be coupled using a variety of different mechanisms known in the art. Referring to FIG. 27, in the illustrated embodiment, apertures $118a_1$, $118a_2$ and $118b_1$, $118b_2$ of cap 28 are aligned with channels 90, 92 of plug 26, However, cap 28 may be oriented in a number of ways relative to plug 26. While plug 26 may be axially aligned with cap 28, it is not necessary for them to be rotationally aligned. Such rotational alignment may make fabrication more costly.

Referring back to FIG. 26, in the illustrated embodiment, apertures $118a_1$, $118a_2$ are oriented around tapered portion 66 of plug 26 such that tapered portion 66 is aligned with apertures $118a_1$, $118a_2$ in the radial direction. Also, in the illustrated embodiment, distal tip 68 of plug 26 is generally adjacent to portions of apertures $118b_1$-$d_2$ and is not adjacent to apertures $118a_1$, $118a_2$ in the radial direction. In other words, in the illustrated embodiment, portions of apertures $118b_1$-$d_2$ are disposed over distal tip 68 of plug 26 in the radial direction. One of ordinary skill in the art will understand, however, that the dimensions of plug 26 relative to cap 28 (and thus of tapered portion 66 and apertures $118a_1$-$d_2$) can vary in accordance with other embodiments.

As illustrated in FIGS. 26-27, each support member 30a-d extends through a pair of diametrically opposed apertures 118a and noses 170a-d of support members 30a-d are disposed in interior 104 of cap 28 distally of distal tip 68 of plug 26 in accordance with some embodiments. Such configuration may constrain movement of noses 170a-d within interior 104 of cap 28. In the illustrated embodiment, radius of curvature 172 (as shown in FIG. 14) of nose 170a of arm 30a (being immediately adjacent to plug 26 in the axial direction) corresponds to tapered portion 66 and radius of curvature 94 of distal tip 68. As such, plug 26 may further be configured to constrain movement of noses 170a-d. At some times during collapse or expansion, nose 170a may rest on tapered portion 66 and/or distal tip 68. At other times, nose 170a may float in apertures $118a_1$, $118a_2$ and not physically contact plug 26, With particular reference to FIG. 26, noses 170a-d of support members 30a-d may overlap along longitudinal axis 24. In the illustrated embodiment, support member 30a is generally oriented in the vertical position and is disposed in the most proximal position; support member 30b is disposed distally of arm 30a and is generally oriented in the horizontal position; support member 30c is disposed distally of support member 30b and is generally oriented 45 degrees clockwise about longitudinal axis 24 from support member 30b (when viewing assembly 12 as illustrated in FIG. 27); and support member 30d is disposed in the most distal position and is generally oriented 45 degrees clockwise about longitudinal axis 24 from support member 30a (when viewing assembly 12 as illustrated in FIG. 27). One of ordinary skill in the art would understand, however, that support members 30a-d may be overlapped in a variety of different ways and extend through various apertures $118a_1$-$d_2$ accordance with other embodiments. Noses 170a-d of support members 30a-d may contact each other at various times during collapse and/or expansion.

Length 120 and width 122 (as shown in FIG. 10A) of apertures $118a_1$-$d_2$ may be designed to accommodate the movement of support members 30a-d (and their noses 170a-d) during expansion and collapse. In some embodiments, apertures $118a_1$-$d_2$ should not be too large to allow noses 170a-d of support members 30a-d to exit interior 104 of cap 28 through apertures $118a_1$-$d_2$. However, apertures $118a_1$-$d_2$ should also not be too small to prevent support members 30a-d from moving freely during expansion and collapse. For example and without limitation, in some embodiments, length 120 of apertures $118a_1$-$d_2$ is 0.030 inches; width 122 of apertures $118a_1$-$d_2$, is 0.0155 inches; a width 228 of support members 30a-d is 0.014 inches; and radii of curvature 174 and 176, 172 of noses 170a-d are 0.025 inches and 0.020 inches, respectively (each measured to the part centerline of support member 30a-d; refer to FIGS. 10A, 14, and 27 for illustration of dimensions). Additionally, the dimensions of apertures $118a_1$-$d_2$ may affect the flow other fluids within the body, such as blood. For example and without limitation, the larger the aperture, the less positive pressure across circumferential wall 110 of cap 28, such that blood may flow inside interior 104 of cap 28. The smaller the aperture, however, the more likely it is that blood will be kept out of interior 104.

Once fluid exits lumen 52 of plug 26, a portion of it contacts support member 30a, which (in the illustrated embodiment) is disposed immediately adjacent of distal tip 68, and travels through channels 90, 92 of distal tip 68. Tapered portion 66, distal tip 68, channels 90, 92, and noses 170a-d of support members 30a-d are designed to allow fluid to exit lumen 52 of plug 26 freely and to not block or imperatively constrain the exit of fluid from lumen 52. For example and without limitation, if width 228 of support member 30a (and thus of nose 170a) was equal to width 97, 99 of channels 90, 92, fluid may be imperatively constrained in lumen 52 (widths 97, 99 shown in FIG. 8), Therefore, in accordance with some embodiments, width 97, 99 of channels 90, 92 may be less than width 228 of support members 30a-d. In accordance with other embodiments, width 97, 99 of channels 90, 92 may be greater than width 228 of support members 30a-d. Fluid may eventually exit interior 104 of cap 28 through apertures 118a₁-d₂.

Although several embodiments have been described above with a certain degree of particularity, those skilled in the art could make numerous alterations to the disclosed embodiments without departing from the scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the disclosure as defined in the appended claims.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While one or more particular embodiments have been shown and described, it will be understood by those of skill in the art that various changes and modifications can be made without departing from the spirit and scope of the present teachings.

What is claimed is:

1. An electrode support structure assembly, comprising:
   a plug defining a longitudinal axis and configured to connect to a fluid delivery line, the plug comprising:
      (i) a lumen configured to receive a fluid from the fluid delivery line, the lumen extending in an axial direction and comprising an axial distal end; and
      (ii) a distal tip adjacent to the axial distal end of the lumen and comprising a first channel extending across the distal tip, wherein the distal tip is substantially rounded with a radius of curvature extending in the axial direction, wherein the distal tip extends in the axial direction such that an apex of the distal tip is at a distalmost end of the plug;
   a cap disposed around and coupled to at least a portion of the plug, the cap comprising:
      (i) a first wall extending in the axial direction and comprising a plurality of apertures; and
      (ii) a second wall extending inwardly from the first wall in a radial direction, the first wall and the second wall defining an interior into which the distal tip of the plug is disposed; and
   a plurality of support members, each of the plurality of support members comprising a distal portion at least partially disposed in the interior of the cap such that the cap is configured to constrain relative movement of the distal portions of the plurality of support members with respect to the cap,
   wherein the first channel of the plug and at least one of the plurality of support members are configured to direct the fluid outwardly in a radial direction after exiting the lumen of the plug; wherein the first channel comprises a semi-rectangular cross-sectional portion; and wherein the first channel is perpendicular to the longitudinal axis of the plug and is configured to direct fluid perpendicularly away from the longitudinal axis of the plug.

2. The assembly of claim 1, wherein the distal portions of the plurality of support members each comprise a nose protruding in the axial direction and are configured to constrain movement thereof in the interior of the cap.

3. The assembly of claim 2, wherein the noses of the distal portions of the plurality of support members overlap along the longitudinal axis.

4. The assembly of claim 2, wherein the at least one of the plurality of support members is configured to at least partially obstruct the fluid after exiting the lumen of the plug.

5. The assembly of claim 2, wherein the at least one of the plurality of support members traverses an entire diameter of the axial distal end of the lumen and the first channel.

6. The assembly of claim 2, wherein the noses of the distal portions of the plurality of support members correspond in shape to at least one of a tapered portion and the distal tip of the plug.

7. The assembly of claim 6, wherein the noses of the distal portions of the plurality of support members correspond in shape along substantially the entire radius of curvature of the distal tip.

8. The assembly of claim 1, wherein the plug is configured to constrain movement of the distal portions of the plurality of support members.

9. The assembly of claim 1, wherein the plurality of apertures are configured to permit the fluid to exit the interior of the cap.

10. The assembly of claim 1, wherein the plug further comprises a second channel configured for directing the fluid after exiting the lumen of the plug.

11. The assembly of claim 10, wherein the first and second channels extend across the distal tip of the plug and the longitudinal axis and are perpendicular to the longitudinal axis, and the second channel is perpendicular to the first channel.

12. The assembly of claim 10, wherein the first channel and the second channel are distal of the axial distal end of the lumen.

13. The assembly of claim 1, wherein the plug further comprises a tapered portion proximal to the distal tip, and the tapered portion is tapered in the axial direction toward the axial distal end of the lumen.

14. The assembly of claim 13, wherein a first and second aperture of the plurality of apertures are aligned with the tapered portion of the plug in a radial direction.

15. The assembly of claim 1, wherein the plurality of apertures are substantially aligned in the axial direction.

16. The assembly of claim 1, wherein the plurality of support members comprises:
- a first support member extending through a first pair of the plurality of apertures of the cap;
- a second support member extending through a second pair of the plurality of apertures of the cap;
- a third support member extending through a third pair of the plurality of apertures of the cap; and
- a fourth support member extending through a fourth pair of the plurality of apertures of the cap.

17. The assembly of claim 16, wherein the first pair, second pair, third pair, and fourth pair of the plurality of apertures are offset from one another in the axial direction.

18. The assembly of claim 1, wherein the plurality of support members are substantially similar in shape and size to one another.

19. The assembly of claim 1, wherein the plurality of support members comprise a first, second, third, and fourth support member, and the distal portions of the plurality of support members comprise:
- a first distal portion of the first support member,
- a second distal portion of the second support member disposed distally of the first distal portion;
- a third distal portion of the third support member disposed distally of the second distal portion; and
- a fourth distal portion of the fourth support member disposed distally of the third distal portion.

* * * * *